United States Patent
Yuhas

(10) Patent No.: US 7,470,056 B2
(45) Date of Patent: Dec. 30, 2008

(54) METHODS AND APPARATUS FOR MONITORING A CONDITION OF A MATERIAL

(75) Inventor: Donald E. Yuhas, Glen Ellyn, IL (US)

(73) Assignee: Industrial Measurement Systems, Inc., Aurora, IL (US)

(*) Notice: Subject to any disclaimer, the term of this patent is extended or adjusted under 35 U.S.C. 154(b) by 147 days.

(21) Appl. No.: 11/056,431

(22) Filed: Feb. 11, 2005

(65) Prior Publication Data
US 2006/0075817 A1 Apr. 13, 2006

Related U.S. Application Data

(60) Provisional application No. 60/543,621, filed on Feb. 12, 2004.

(51) Int. Cl.
*G01K 13/00* (2006.01)
*G01K 11/22* (2006.01)
*G01N 25/00* (2006.01)

(52) U.S. Cl. .................... 374/7; 374/119; 374/141; 374/45

(58) Field of Classification Search ............. 374/119, 374/7, 45, 141
See application file for complete search history.

(56) References Cited

U.S. PATENT DOCUMENTS

| | | | |
|---|---|---|---|
| 2,829,185 A | 4/1958 | Macatician et al. | |
| 3,231,387 A | 1/1966 | Tsuchiya et al. | |
| 3,618,455 A | 11/1971 | Plumer et al. | |
| 3,921,499 A | 11/1975 | Ginsky | |
| 4,353,256 A | 10/1982 | Moorey | |
| 4,513,749 A | 4/1985 | Kino et al. | |
| 4,567,747 A * | 2/1986 | Matay | 73/597 |
| 5,016,474 A * | 5/1991 | Hazony et al. | 73/597 |

(Continued)

FOREIGN PATENT DOCUMENTS

GB 2 328 498 2/1999

(Continued)

OTHER PUBLICATIONS

M.I.T. Computer Science and Artificial Intelligence Laboratory, *The Cricket Indoor Location System*, http://nms.lcs.mit.edu/projects/cricket/, Aug. 19, 2005.

(Continued)

*Primary Examiner*—Edward Lefkowitz
*Assistant Examiner*—Mirellys Jagan
(74) *Attorney, Agent, or Firm*—Hanley, Flight & Zimmerman, LLC

(57) ABSTRACT

Apparatus, methods, and articles of manufacture for monitoring a condition of a cavity surface of an elongated member having a cavity therein. In particular, the example apparatus, methods, and articles of manufacture emit a first ultrasonic signal that propagates from a first surface of an elongated member having a cavity therein toward a second surface of the cavity having a first temperature value. First and second echoes associated with the first ultrasonic signal are then obtained. At least one of the first and second echoes is associated with a recess in the second surface. A condition of the second surface is monitored by determining a second temperature value of the second surface based on the first and second echoes and the first temperature value.

27 Claims, 14 Drawing Sheets

U.S. PATENT DOCUMENTS

| | | | |
|---|---|---|---|
| 5,182,139 | A | 1/1993 | Frankel et al. |
| 5,214,955 | A | 6/1993 | Yost et al. |
| 5,293,131 | A | 3/1994 | Semones et al. |
| 5,347,909 | A | 9/1994 | Kozlik |
| 5,469,742 | A | 11/1995 | Lee et al. |
| 5,557,970 | A | 9/1996 | Abbate et al. |
| 5,659,148 | A | 8/1997 | Isgen |
| 6,378,372 | B1 | 4/2002 | Karr |
| 6,481,287 | B1 | 11/2002 | Ashworth et al. |
| 6,587,213 | B1 | 7/2003 | Knight et al. |
| 6,815,701 | B2 | 11/2004 | Schlenkert et al. |
| 6,834,992 | B2 | 12/2004 | Draxton et al. |
| 6,968,727 | B2 * | 11/2005 | Kwun et al. ............ 73/1.82 |
| 7,404,671 | B2 | 7/2008 | Heyman et al. |
| 2002/0078752 | A1 * | 6/2002 | Braunling et al. ............ 73/627 |
| 2003/0167909 | A1 | 9/2003 | Matter |
| 2004/0211261 | A1 | 10/2004 | Prause |

FOREIGN PATENT DOCUMENTS

| | | | |
|---|---|---|---|
| JP | 61038433 | | 2/1986 |
| JP | 01203967 | A * | 8/1989 |
| JP | 10127632 | | 5/1998 |
| JP | 2001074567 | | 3/2001 |

OTHER PUBLICATIONS

Baharis, C., and Comish, R., 1991. "Ultrasonic Detection of Heat Fronts in Continuously Cast Steel Product". IEEE, In Proceedings of the Ultrasonics Symposium, vol. 2, pp. 957-960.

Hoyle et al., "Ultrasound in the Process Industries," Engineering Science and Education Journal, vol. 3, Issue 3, pp. 119-122, Jun. 1994.

Yee et al., "Application of Ultrasound to NDE of Materials," IEEE Transactions on Sonics and Ultrasonics, vol. SU-23, Issue 5, pp. 299-305, IEEE Sep. 1976.

Liu, John M., "Temperature Dependence of Elastic Stiffness in Aluminum Alloys Measured with Non-Contact Electromagnetic Acoustic Transducers (Emats)," 1984 Ultrasonics Symposium, pp. 972-974, IEEE 1984.

Livengood et al., "Ultrasonic Temperature Measurement in Internal Combustion Engine Chamber," The Journal of the Acoustical Society of America, vol. 26, Issue 5, pp. 824-830, Sep. 1954.

Duncombe, Edward, "Some Instrumental Techniques for Hostile Environments," J. Phys. E: Sci. Instrum., vol. 17, pp. 7-18, The Institute of Physics, 1984.

Lu et al., "Acoustic Computer Tomographic Pyrometry for Two-Dimensional Measurement of Gases Taking Into Account the Effect of Refraction of Sound Wave Paths," Meas. Sci. Technol., U.K., vol. 11, Issue 6, pp. 692-697, IOP Publishing Ltd., Jun. 2000.

Mi et al., "Automatic Ultrasonic Thermometry," 2003 Fifteenth Symposium on Thermophysical Properties, Boulder, CO, USA, Jun. 22, 2003 (9 pages).

Liao et al., "A New Ultrasonic Temperature Measurement System for Air Conditioners in Automobiles," Meas. Sci. Technol., vol. 15, Issue 2, pp. 413-419, Institute of Physics Publishing, U.K., Dec. 19, 2003.

Tsai et al., "An Ultrasonic Air Temperature Measurement System with Self-Correction Function for Humidity," Meas. Sci. Technol., vol. 16, Issue 2, pp. 548-555, Institute of Physics Publishing, U.K., Jan. 21, 2005.

Carnevale et al., "Experimental Determination of Transport Properties of High Temperature Gases," NASA CR-789, National Aeronautics and Space Administration, Washington, D.C., USA, Jun. 1967 (124 pages).

Chen, G., "Phonon Wave Heat Conduction in Thin Films and Superlattices," Journal of Heat Transfer, vol. 121, Nov. 1999, pp. 945-953.

Green, S. F., "An Acoustic Technique for Rapid Temperature Distribution Measurements," Journal of the Acoustical Society of America, 77(2), Feb. 1985, pp. 759-763.

Fife, S., Andereck, C. D., and Rahal, S., "Ultrasound Thermometry in Transparent and Opaque Fluids," Experiments in Fluids, 35, 2003, pp. 152-158.

Wadley, H. N. G., Norton, S. J., Mauer, F., Droney, B., Ash, E. A., and Sayers, C.M., "Ultrasonic Measurement of Internal Temperature Distribution," Philosophical Transactions of the Royal Society of London, Series A, Mathematical and Physical Sciences, 320(1554), Nov. 1986, pp. 341-361.

Chen, G., "Phonon Wave Heat Conduction in Thin Films and Superlattices," Journal of Heat Transfer, vol. 121, Nov. 1999, pp. 945-953.

Green, S. F., "An Acoustic Technique for Rapid Temperature Distribution Measurements," Journal of the Acoustical Scoiety of America, 77(2), Feb. 1985, pp. 759-763.

Fife, S., Andereck, C. D., and Rahal, S., "Ultrasound Thermometry in Transparent and Opaque Fluids," Experiments in Fluids, 35, 2003, pp. 152-158.

Wadley, H. N. G., Norton, S. J., Mauer, F., Droney, B., Ash, E. A., and Sayers, C.M., "Ultrasonic Measurement of Internal Temperature Distribution," Philosophical Transactions of the Royal Society of London, Series A, Mathematical and Physical Science, 320(1554), Nov. 1986, pp. 341-361.

* cited by examiner

US 7,470,056 B2

METHODS AND APPARATUS FOR MONITORING A CONDITION OF A MATERIAL

RELATED APPLICATION

This patent incorporates by reference herein in its entirety and claims the benefit of provisional U.S. Patent Application No. 60/543,621, filed Feb. 12, 2004.

The invention was made with Government support under contract number N00178-03-C-1081 awarded by the United States Department of Defense to Industrial Measurement Systems, Incorporated, and is based upon work supported by the Naval Surface Warfare Center, Dahlgren Division. The Government has certain rights in the invention. Work related to the invention was also supported by the Government under contract number N00178-04-C-1070.

FIELD OF THE DISCLOSURE

The present disclosure relates generally to monitoring a material condition and, more particularly, to methods and apparatus for non-invasively monitoring a condition of a material.

BACKGROUND

Monitoring operating conditions in commercial or industrial applications is often crucial to maintaining proper and safe operation of machinery. Material temperature and material erosion (e.g., material wear, material breakdown, etc.) are two conditions that can affect the performance of machines, apparatus, or systems. Continuous operation or repeated use often elevates the temperature of machines or apparatus. Uncontrolled or overly elevated temperatures may impair the operation of the machine or apparatus. In a similar manner, continuous operation causes material erosion, material wear, material breakdown, etc. of portions of a machine, system, or apparatus. For example, as a fluid flows through an inner bore of a fluid vessel (e.g., a pipe) the fluid causes small particles to break away from the fluid vessel's inner bore surface, which causes the inner bore of the fluid vessel to erode over time. Left unmonitored and/or untreated, such material erosion can lead to unsafe conditions and failure conditions in the machine, system, or apparatus.

The military has similar concerns as those of commercial or industrial entities regarding material conditions such as temperature and erosion. In particular, the military recognizes that operating conditions, such as temperature and erosion, affect the performance and the safe and proper operation of munitions (e.g., weapons). For example, during training exercises and combat scenarios, large caliber guns (e.g., a 5-inch/62-caliber (5"/62) EX 36 MOD 0 gun barrel) installed on Navy ships are often subjected to continuous and repeated operation. To ensure safe and proper operation of the guns, a gun crew must ensure that gun barrels operate within safe operating conditions. Accordingly, the Navy has a critical need to monitor the temperatures at critical areas on the inner bore surfaces of large guns so that a gun crew can act appropriately in cases of misfire. More specifically, in the case of a misfire, the gun crew must know the temperature of the gun barrel bore surface to determine if there is enough time to safely reload the gun (e.g., open the breech, remove the ammunition from the hot gun barrel, and replace the projectile or propelling charge) and fire another projectile or propelling charge before enough heat has transferred from the hot barrel to the projectile. Heat transfer from the gun barrel to the projectile may initiate a cook-off of the projectile, which can result in a misfire.

Traditional methods of determining the temperature of a gun barrel involve using a simplistic chart known as a hot-gun predictor. The hot-gun predictor chart was originally developed for the 5"/54 MK 45 MOD 2 gun, but is often used with other gun types. However, when advanced projectiles and higher energy propelling charges are used, results obtained during gun firing tests and from thermal modeling suggest that the hot gun predictor chart may be either excessively conservative or very non-conservative depending on operating conditions or other circumstances prior to a misfire. Thus, the results from these tests indicate that the hot-gun predictor chart is not well-adapted for use when variables such as ammunition-type are changed.

In a similar manner, measuring erosion of a gun barrel bore surface is often done via predictions and estimates generated using material modeling techniques. More specifically, the material properties (e.g., strength, hardness, etc.) and the shapes of gun barrels and projectiles may be used to model or calculate the rate of erosion of a gun barrel bore based on a number of fired projectiles. Although such modeling techniques can be used to estimate the amount or rate of erosion, the actual erosion often differs due to many factors such as, for example, variations in material, the periodicity of firing, environmental factors (e.g., humidity, ambient temperature, etc.), etc.

Although some measurement or monitoring systems have been developed to measure the temperatures of gun barrel bores, many of those systems are invasive and require access to the gun barrel bore when it is at elevated temperatures. For example, some systems require inserting a thermocouple into the gun barrel bore to obtain a temperature reading. Accessing a gun barrel bore when it is at an elevated temperature is often dangerous and time consuming. In addition, some measurement systems are more suited to operate in an academic or laboratory environment, but may be impractical or cumbersome for use in a real-world environment.

DETAILED DESCRIPTION

Figure 1:
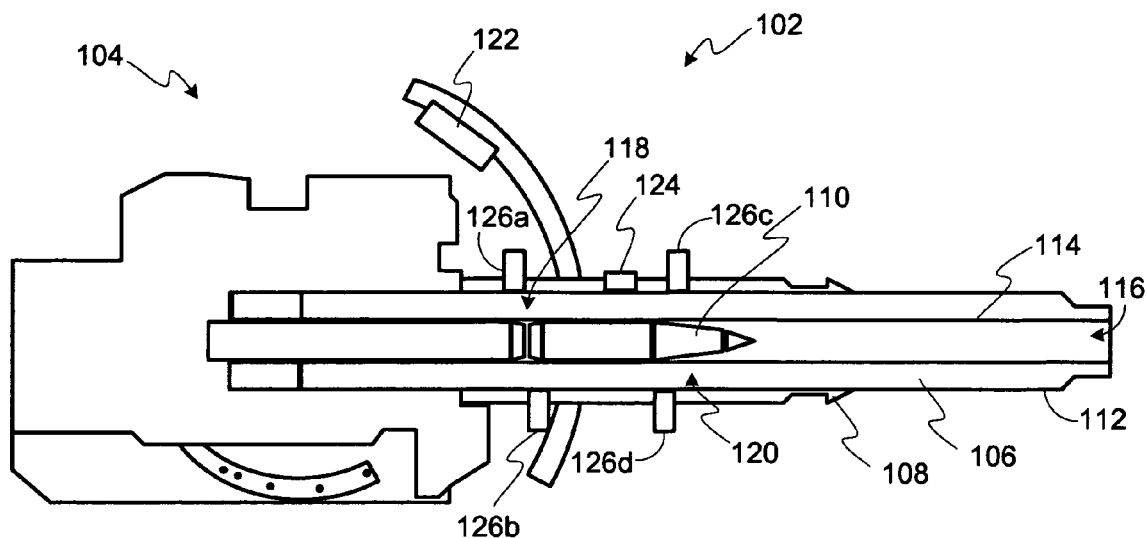
FIG. 1 illustrates an example large caliber gun having an example temperature and erosion monitoring system mounted thereto.

Although the following discloses example systems including, among other components, software executed on hardware, it should be noted that such systems are merely illustrative and should not be considered as limiting. For example, it is contemplated that any or all of these hardware and software components could be embodied exclusively in hardware, exclusively in software, or in any combination of hardware and software. Accordingly, while the following describes example systems, persons having ordinary skill in the art will readily appreciate that the examples provided are not the only way to implement such systems.

In general, the example methods, systems, and apparatus described herein may be used to monitor temperature and erosion in a non-invasive manner of gun barrels and other elongated members having a pipe-like or tubular structure. More generally, the example methods, systems, and apparatus may be used to monitor temperature and erosion conditions associated with a cavity surface (e.g., a bore surface) of an elongated member. As described in greater detail below, the example methods, systems, and apparatus may be implemented using acoustic measurement techniques (e.g., ultrasonic measurement techniques) and used in combination with gun barrels or other elongated pipe-like, tubular, or cylindrical members in a field environment. For example, the example systems and apparatus described herein may be mounted to a gun barrel, tubular article, a pipe-like article, cylindrical members, etc. and may monitor temperature and erosion associated with cavity surfaces or bore surfaces during operation of the gun barrel, the tubular article, the pipe-like article, etc. Although the example methods, systems, and apparatus described herein may be more generally applied to measure gun barrels and other elongated tubular or cylindrical members, for purposes of clarity, the example methods, systems, and apparatus are described below with respect to gun barrels. More specifically, the gun barrels described below are large caliber gun barrels such as, for example, 5-inch/62-caliber (i.e., 5"/62) EX 36 MOD 0 gun barrels, which may be configured to be mounted on naval ships.

As described in greater detail below, the example methods, systems, and apparatus may be implemented using any acoustic technology capable of propagating an acoustic signal through a solid material such as, for example, steel. Ultrasound is an example acoustic measurement technology that is capable of transmitting compressional wave signals and shear wave signals through a solid material. A compressional wave (i.e., a longitudinal wave, a P-wave) propagates through a material by displacing particles in a direction parallel to the direction in which the compressional wave propagates. A shear wave (i.e., a transverse wave, an S-wave) propagates through a material by displacing particles in a direction perpendicular to the direction in which the shear wave propagates. An example temperature and erosion monitoring system (e.g., the example temperature and erosion monitoring system 102 of FIGS. 1 and 2) is configured to emit acoustic signals (e.g., ultrasonic waves) into a gun barrel wall and receive echoes associated with the acoustic signals after the acoustic signals are reflected by one or more surfaces of the gun barrel bore. The example system determines propagation times associated with the propagation of the acoustic signal and then determines the temperature of the gun barrel near the gun barrel bore surface and/or an amount of erosion of the gun barrel bore surface based on the propagation times.

FIG. 1 illustrates a large caliber gun 104 having an example temperature and erosion monitoring system 102 mounted thereon. The large caliber gun 104 (e.g., the gun 104) is configured to fire large caliber ammunitions or projectiles and may be configured to be mounted onto naval ships, terrestrial vehicles, or any other transport. Alternatively, the gun 104 may be a stand-alone gun that is grounded in a stationary location at, for example, a military base or outpost. The example temperature and erosion monitoring system 102 (i.e., the monitoring system 102) may be used to implement the example methods, systems, and apparatus described herein. The monitoring system 102 measures temperature and erosion associated with the gun 104 based on acoustic measurement techniques using, for example, ultrasonic technologies. The monitoring system 102 may be mounted to the gun 104 as shown in FIG. 1 to enable the monitoring system 102 to acquire acoustic measurement information as acoustic signals are emitted into portions of the gun 104.

The gun 104 includes a gun barrel 106 and a slide cylinder 108, which are configured to work cooperatively to launch or fire a projectile 110 (i.e., a round, ammunition, etc.). The gun barrel 106 is an elongated member that includes an outer surface 112 and a gun barrel bore surface 114 (e.g., a cavity surface). The gun barrel bore surface 114 forms a gun barrel bore 116 (e.g., a cavity) configured to receive and guide the projectile 110. The gun barrel bore surface 114 is smooth at the loading end of the gun barrel 106, and is rifled toward the exit end of the gun barrel 106. More specifically, as shown in FIG. 1, the gun barrel bore surface 114 includes a non-rifled surface portion (i.e., a smooth surface portion) generally indicated by reference numeral 118 (i.e., the non-rifled portion 118) and a rifled surface portion generally indicated by reference numeral 120 (i.e., the rifled portion 120). The gun barrel bore surface 114 at the rifled portion 120 is shown in greater detail in FIG. 3. The slide cylinder 108 is configured to receive the gun barrel 106 therein and, amongst other functions, serve as a linear guide for the gun barrel 106 as the gun barrel 106 recoils during a firing process.

The monitoring system 102 includes a base system 122, a temperature transducer 124, and a plurality of acoustic transducers 126. The system 102 is described in greater detail below in connection with FIG. 3. As shown in FIG. 1, the base system 122 may be mounted to a portion of the gun 104 some distance away from the temperature transducer 124 and the acoustic transducers 126. The temperature transducer 124 and the acoustic transducers 126 may be mounted to the gun barrel 106 and configured to communicate temperature related information and acoustic measurement related information to the base system 122. In one example, the temperature transducer 124 and the acoustic transducers 126 may be mounted to the gun barrel 104 by notching, machining, or otherwise forming holes or openings (e.g., not shown) in the slide cylinder 108, inserting the transducers 124 and 126 through the openings, and coupling the transducers 124 and 126 to the outer surface 112 of the gun barrel 106. The openings may be elongated along the length of the slide cylinder 108 to allow the transducers 124 and 126 to move freely with respect to the slide cylinder 108 as the gun barrel 106 recoils within the slide cylinder 108.

The temperature transducer 124 is used for calibrating the system 102 during times when the gun 104 is not being fired and/or the gun barrel 106 has reached an isothermal condition. The gun barrel 106 may be in an isothermal condition with respect to space (e.g., the space within a material volume) and/or time. For example, the gun barrel 106 may be in an isothermal condition when substantially no temperature gradients exist in the gun barrel 106 and the temperature of the gun barrel 106 is substantially uniform throughout the gun barrel 106. The gun barrel 106 may also be in an isothermal condition when the temperature of the gun barrel 106 is constant or the same for a relatively long time period.

The temperature transducer 124 may be used to measure an isothermal temperature of the gun barrel 106. As described below, the isothermal temperature may be used to determine a gun barrel temperature near the gun barrel bore surface 114 during operation of the gun barrel 106 (e.g., during firing regiments, when the gun barrel 106 is in a non-isothermal condition, etc.). As is also described below, the isothermal temperature may also be used to determine an amount of erosion of the gun barrel bore surface 114. The temperature transducer 124 may be placed as close as possible (e.g., within millimeters, abutting, etc.) to one of the acoustic transducers 126. In this manner, during isothermal conditions or while testing for an isothermal condition the temperature transducer 124 may acquire a temperature value that most closely represents the temperature of the gun barrel 106 at the location of one of the transducers 126. Although one temperature transducer is shown, more or fewer temperature transducers may be used. For example, one example implementation may include four temperature transducers, each of which may be placed adjacent to one of the acoustic transducers 126.

Each of the acoustic transducers 126 may be used for a particular measurement. The acoustic transducer 126a may be used to measure temperature and the acoustic transducer 126b may be used to measure erosion at the non-rifled portion 118. The acoustic transducer 126c may be used to measure temperature and the acoustic transducer 126d may be used to measure erosion at the rifled portion 120. Although four acoustic transducers 126 are shown, more or fewer transducers may be used. For example, an alternative example implementation may include two acoustic transducers. A first transducer may be used to measure both temperature and erosion at the non-rifled portion 118 and a second transducer may be used to measure both temperature and erosion at the rifled portion 120.

As described in greater detail below, the monitoring system 102 is calibrated prior to monitoring the temperature and erosion of the gun barrel 106. Specifically, the monitoring system 102 is calibrated by emitting acoustic signals into the gun barrel 106 and measuring propagation times of the acoustic signals during an isothermal condition of the gun barrel 106. The monitoring system 102 emits and detects the acoustic signals using the transducers 126 to measure propagation times associated with the amount of time required by the acoustic signals to propagate through a wall of the gun barrel 106 (e.g., the gun barrel wall 306 of FIG. 3) or a rifling element (e.g., one of the rifling elements 302 of FIG. 3). In some cases, prior to calibrating the monitoring system 102, the monitoring system 102 may use the temperature transducer 124 to ensure that the gun barrel 106 is in an isothermal condition by, for example, measuring the temperature of the outer surface 112 and ensuring that the temperature indicates an isothermal condition. An example method that may be used to determine if the gun barrel 106 is in an isothermal condition is described in greater detail below in connection with FIGS. 13 and 15. As described below, an isothermal temperature of the gun barrel 106 may be used as a calibration temperature $T_C$ that may be subsequently used to monitor the temperature and erosion of the gun barrel 106.

Figure 2:
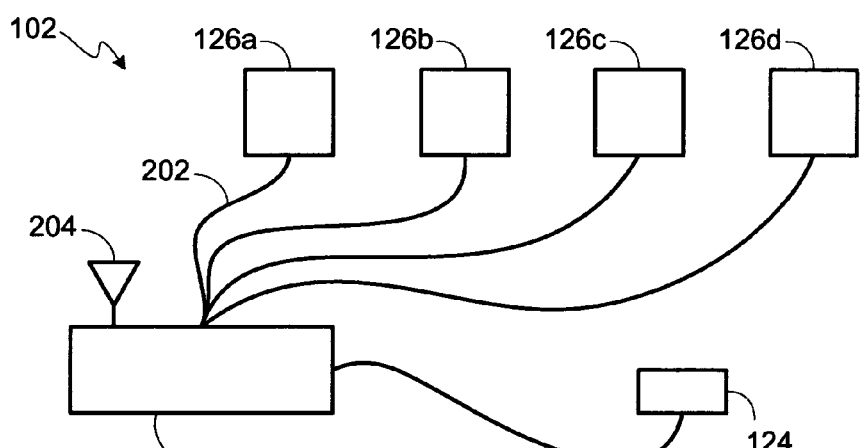
FIG. 2 illustrates a detailed diagram of the example temperature and erosion monitoring system of FIG. 1.
Figure 2:
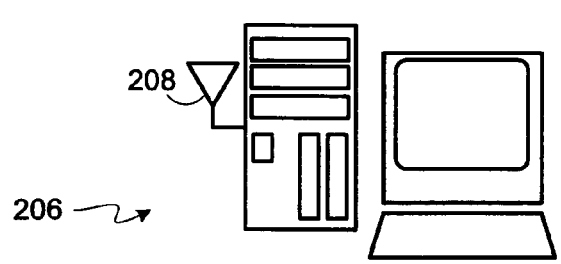

FIG. 2 illustrates a detailed diagram of the example temperature and erosion monitoring system 102 of FIG. 1. Each of the transducers 124 and 126 is communicatively coupled to the base system 122 via wires or cables 202. The base system 122 may control the emission and reception of signals associated with each of the transducers 124 and 126 via the wires 202. For example, the base system 122 may control the triggering or emission timing of the acoustic transducers 126 so that the acoustic transducers 126 can emit acoustic signals (e.g., ultrasound signals or waves) into the gun barrel 106 and subsequently detect echoes associated with each of the emitted acoustic signals. Specifically, the base system 122 may generate an electrical signal having a specified frequency (e.g., an ultrasonic frequency), communicate via the wires 202 the electrical signal to the acoustic transducers 126, which then emit an acoustic signal into the gun barrel 106 based on the electrical signal. The acoustic transducers 126 can subsequently detect acoustic echoes associated with the emitted acoustic signal, convert the echoes into electrical signals, and communicate the electrical signals to the base system 122 via the wires 202.

Figure 21:
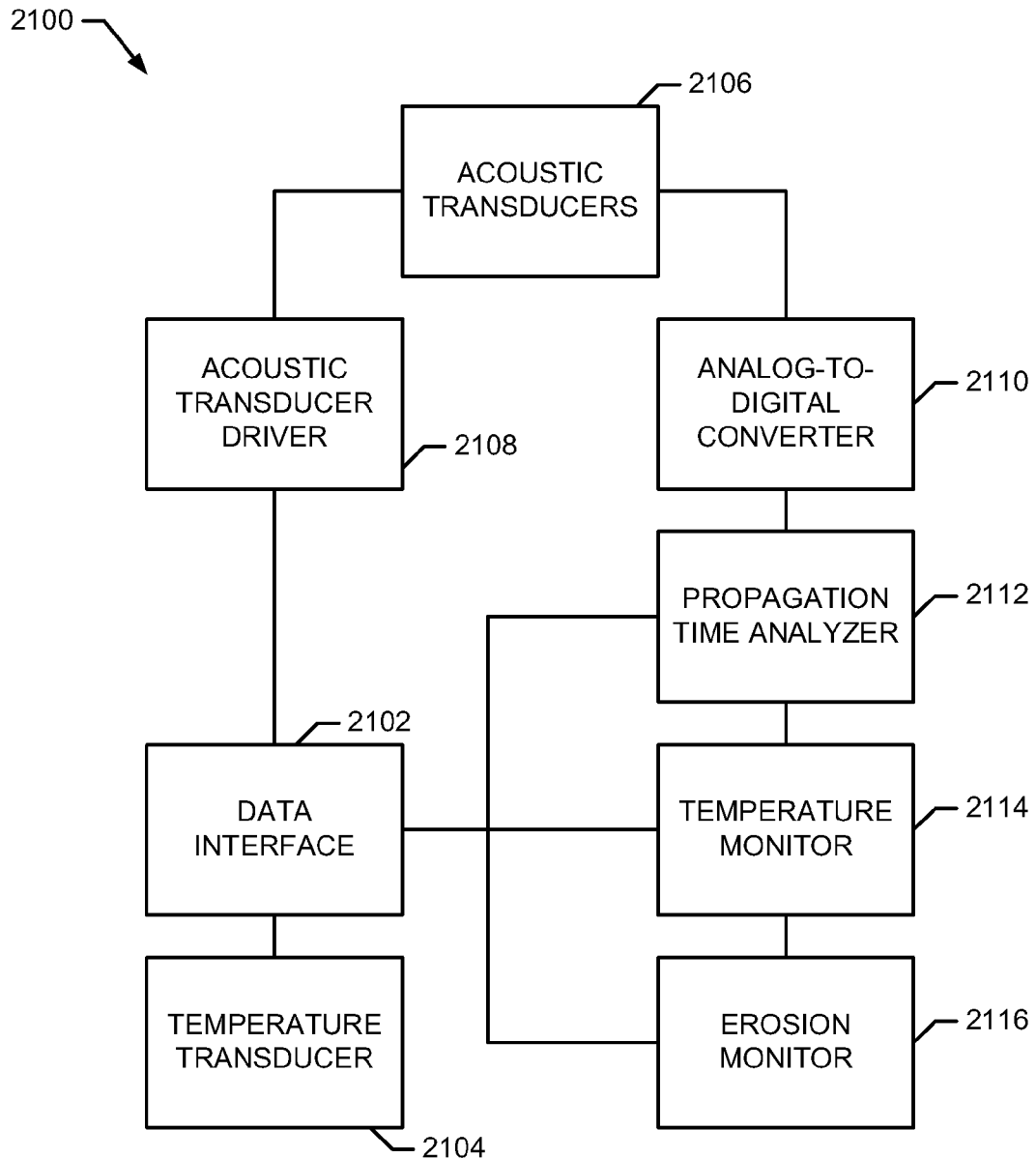
FIG. 21 is a functional block diagram of an example system that may be used to implement the apparatus, methods, and articles of manufacture described herein.

The base system 122 may include a processor system (e.g., the processor system 2210 of FIG. 22) and/or a dedicated hardware system (e.g., a hardware system implemented based on the example system 2100 of FIG. 21) and may be configured to obtain information associated with acoustic signal emissions into portions of the gun barrel 106 that are then used to monitor the temperature and erosion of the gun barrel 106. The temperature transducer 124 may be implemented using any suitable temperature transducer such as, for example, a thermocouple, an infrared temperature sensor, etc. The acoustic transducers 126 may be implemented using transducers configured to emit and receive ultrasonic signals. For example, each of the acoustic transducers 126 may be implemented using a piezoelectric transducer, which is a common type of ultrasonic transducer. Piezoelectric transducers operate based on the piezoelectric effect which has bi-directional electrical field generation properties. More specifically, a varying voltage applied across a plate or disc may generate an ultrasonic field. Conversely, an ultrasonic pulse impinging on a piezoelectric crystal will result in a voltage or an electrical charge being generated across the surface of the plate or disc.

Ultrasound includes frequencies in the megahertz (MHz) range, which are highly attenuated in air. To reduce or substantially eliminate attenuation of ultrasound signals, piezoelectric transducers are typically directly coupled to a surface (e.g., the outer surface 112 of the gun barrel 106). A piezoelectric transducer may be directly bonded to the surface by, for example, welding the transducer to the surface, bonding the transducer to the surface using epoxy or other means, integrally forming the transducer with the surface, etc. Alternatively, a piezoelectric transducer may be coupled to the surface via a coupling fluid (e.g., water, glycerin, or any other suitable high temperature coupling material) by disposing the coupling fluid between the piezoelectric transducer and the surface. In this manner, any air gaps or air pockets between the piezoelectric transducer and the surface are minimized or substantially eliminated.

Transducers (e.g., the transducers 124 and 126) may be coupled to the gun 104 to accommodate the recoil motion of the gun barrel 106 during a firing process. Specifically, as noted above, the gun barrel 106 moves relative to the slide cylinder 108. To accommodate the recoil motion, the transducers 124 and 126 may be coupled to the slide cylinder 108 or to the gun barrel 106. For example, the transducers 124 and 126 may be fixedly coupled to the slide cylinder 108 and slidably coupled to the outer surface 112 of the gun barrel 106. In this case, as the gun barrel 106 recoils, the transducers 124 and 126 can slide along the outer surface 112 of the gun barrel 106. Alternatively, the transducers 124 and 126 may be fixedly coupled to the gun barrel 106. In this case, material may be removed (e.g., notched, machined, cut, etc.) from the slide cylinder 108 to ensure that the transducers 124 and 126 can move freely relative to the slide cylinder 108 so that the slide cylinder 108 does not interfere with the transducers 124 and 126 when the gun barrel 106 recoils during a firing regiment.

The acoustic transducers 126 may also be implemented using non-contact ultrasonic technologies. Some example non-contact ultrasonic technologies include laser generation devices, Electromagnetic Acoustic Transduction (EMAT) devices, and spark gap devices. Some non-contact ultrasonic technologies include separate or discrete receivers and transmitters. Non-contact ultrasonic receivers include interferometers for use with laser generation devices, capacitive receivers, and EMAT receivers. Even though the signal processing to extract or determine timing information (e.g., the propagation times) associated with the emission and reception of ultrasonic signals may be different for each ultrasonic technology, the example methods, systems, and apparatus described herein may be adapted accordingly.

Implementing the example methods, systems, and apparatus at elevated temperatures may require operating piezoelectric sources under conditions that exceed their specified temperature limits. In piezoelectric ceramics the Curie temperature can range from 300° F. to 1000° F. If the example methods, systems, and apparatus are implemented at elevated temperatures, the acoustic transducers 126 may be implemented using high temperature piezoelectric crystals such as quartz, lithium niobate, etc. Additionally, piezoelectric transducers can by thermally isolated and/or implemented in combination with buffers or delay lines as is commonly practiced by those skilled in the art of high temperature ultrasonic testing.

As shown in FIG. 2, the base system 122 includes an antenna 204. The antenna 204 may be used to communicate information between the base system 122 and a central processing system 206 having another antenna 208. The antennas 204 and 208 enable the base system 122 and the central processing system 206 to be wirelessly communicatively coupled using any suitable wireless protocol such as, for example, 802.11 (i.e., Wi-Fi®), Bluetooth®, 900 MHz, etc. Alternatively, although not shown, the base system 122 may be communicatively coupled via a cable or a wire to the central processing system 206 or any other processing system (e.g., a gun control system, a ship control system, etc.).

In an example implementation, the base system 122 may be configured to perform all signal processing operations associated with the acoustic signals to determine temperature and erosion measurements. The base system 122 may also store all of the resultant values in a locally stored database and periodically or immediately communicate the values to the central processing system 206. In this manner, a gun crew may obtain temperature and erosion information from the central processing system 206. The central processing system 206 may be integral or communicatively coupled with the control system of the gun 104 or a naval ship, terrestrial vehicle, or any other transport onto which the gun 104 is mounted. The central processing system 206 may generate historical databases that may be used to perform long-term analysis of the gun 104 for purposes of, for example, performance analysis, maintenance analysis, replacement analysis, etc. The central processing system 206 may be implemented using the example processor system 2210 of FIG. 22.

Figure 3:
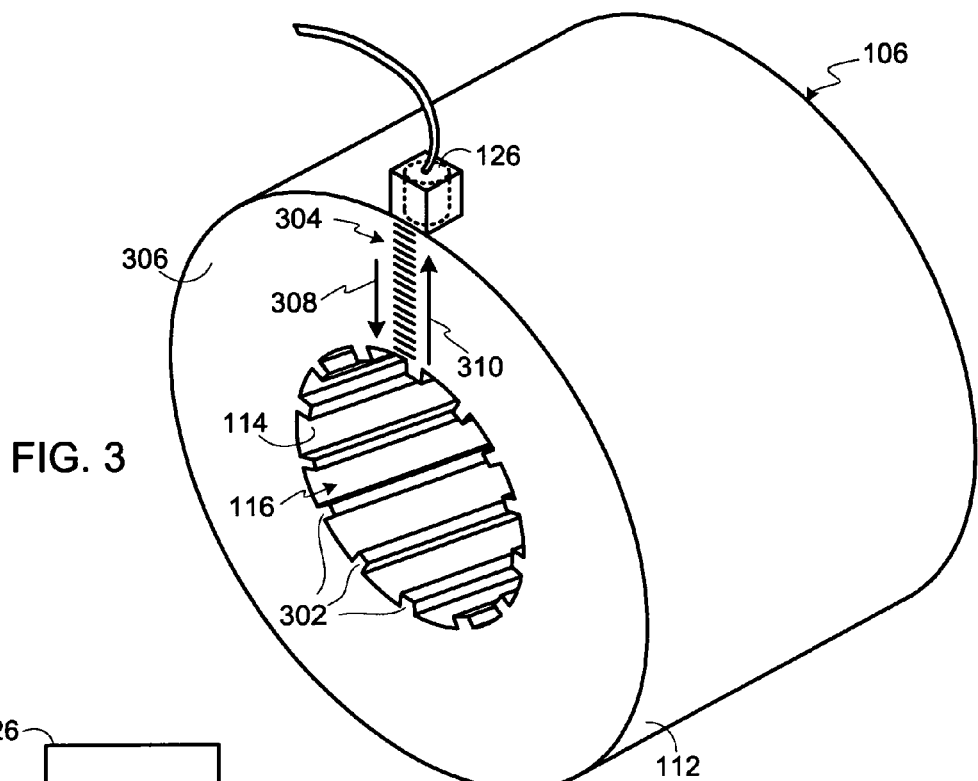
FIG. 3 illustrates an acoustic transducer mounted to an outer surface of a gun barrel.

FIG. 3 illustrates an acoustic transducer (e.g., one of the acoustic transducers 126 of FIGS. 1 and 2) mounted to an outer surface of a gun barrel (e.g., the outer surface 112 of the gun barrel 106 of FIG. 1). More specifically, the acoustic transducer 126 is coupled to the outer surface 112 at a location where the acoustic transducer 126 can emit acoustic signals toward the gun barrel bore surface 114 at the rifled portion 120 of the gun barrel 106. As shown in FIG. 3, the gun barrel bore surface 114 at the rifled portion 120 includes rifling elements 302 that are formed along the length of the gun barrel 106. Although not shown, one of the acoustic transducers 126 may be coupled to the outer surface 112 at a location associated with the non-rifled portion 118 of the gun barrel 106 in a manner substantially similar to one of the acoustic transducers 126 coupled to the outer surface 112 at the rifled portion 120.

In general, FIG. 3 depicts how the acoustic transducer 126 may be used to emit an acoustic signal 304 (e.g., an ultrasonic signal) into the gun barrel 106 and detect acoustic echoes associated with the acoustic signal. As shown in FIG. 3, the acoustic transducer 126 is configured to emit the acoustic signal 304 into a gun barrel wall 306 from the outer surface 112 toward the gun barrel bore surface 114. The acoustic signal 304 propagates toward the gun barrel bore surface 114 in a direction generally indicated by arrow 308 and is reflected by the gun barrel bore surface 114 to produce one or more echoes as described in greater detail below in connection with FIGS. 4 and 5. The echoes propagate toward the outer surface 112 in a direction generally indicated by arrow 310 and may be detected by the acoustic transducer 126, which may then convert the one or more echoes into electrical signals that are communicated to the base system 122 (FIG. 1).

Figure 4:
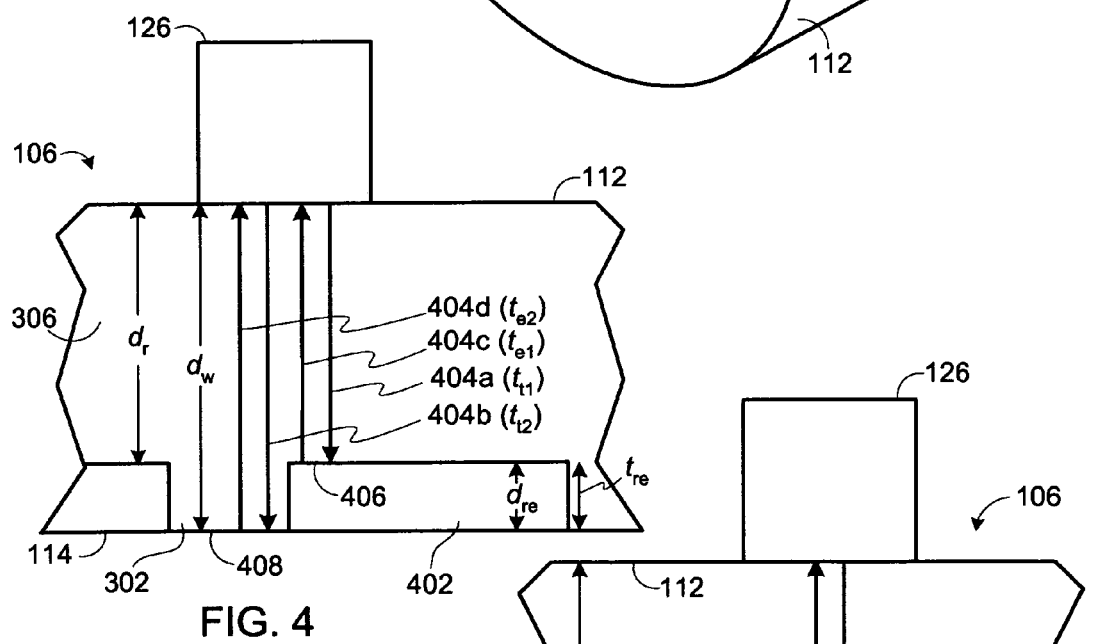
FIG. 4 is a partial view of the gun barrel with the acoustic transducer coupled thereto that is configured to emit acoustic signals into the rifled portion of the gun barrel.

FIG. 4 is a partial view of the gun barrel 106 with the acoustic transducer 126 coupled thereto that is configured to emit acoustic signals (e.g., the acoustic signal 304 of FIG. 3) into the rifled portion 120 of the gun barrel 106. As shown, the gun barrel bore surface 114 at the rifled portion 120 includes the rifling element 302 and a recess 402 (e.g., a channel) adjacent to the rifling element 302. The acoustic transducer 126 is configured to emit acoustic signals that propagate in the gun barrel wall 306 along directions generally indicated by arrows 404a and 404b and then detect acoustic echoes that travel along directions generally indicated by the arrows 404c and 404d. In this manner, the base system 122 (FIG. 1) can determine propagation times associated with the acoustic signals to then determine the temperature near the gun barrel bore surface 114 and erosion of the gun barrel bore surface 114.

The monitoring system 102 is configured to determine a gun barrel temperature near the gun barrel bore surface 114 by determining an average temperature of the rifling element 302 based on acoustic signal propagation times. Specifically, during a firing regiment the temperature of the gun barrel 106 increases and thermal gradients are generated in the gun barrel wall 306 and the rifling elements 302. The thermal gradients are generated because the temperature of the gun barrel 106 near the gun barrel bore surface 114 increases at a faster rate than the temperature of the gun barrel 106 near the outer surface 112. Although the thermal gradients may cause the gun barrel temperature near the outer surface 112 to be substantially different than the temperature of the gun barrel bore surface 114, the methods, systems, and apparatus described herein may be used to approximate a temperature of the gun barrel bore surface 114 based on an average temperature of thermal gradients that may be present in the rifling elements 302 and/or an average temperature of thermal gradients that may be present in the gun barrel wall 306.

In the rifled portion 120, the effects of thermal gradients in the gun barrel wall 306 on temperature measurements near the gun barrel bore surface 114 may be substantially eliminated by approximating the temperature of or near the gun barrel bore surface 114 based on an average temperature of the rifling element 302 (i.e., a local temperature of the rifling element 302). In other words, the temperature of the gun barrel bore surface 114 may be reasonably approximated to a relatively high degree of accuracy by determining the average temperature of the rifling element 302. Although the rifling elements 302 may have thermal gradients, a typical rifling element thickness $d_{re}$ is about 0.050". A thermal gradient in the rifling element thickness $d_{re}$ will be relatively small and, thus, the difference in temperature between the gun barrel bore surface 114 and an average temperature of the rifling element 302 will be negligible or substantially zero.

In the non-rifled portion 118 of the gun barrel 106, the temperature of the gun barrel bore surface 114 may be reasonably approximated by determining an average temperature of the gun barrel wall 306 using the example methods described herein. Of course, because the gun barrel wall 306 may have relatively larger thermal gradients than the rifling element 302, in some cases (e.g., under non-isothermal conditions of the gun barrel 106) the average temperature of the rifling element 302 may be a relatively better approximation of the temperature of the gun barrel bore surface 114 than the average temperature of the gun barrel wall 306.

When the gun barrel 106 is in an isothermal condition, thermal gradients in the rifling elements 302 and the gun barrel wall 306 will be substantially eliminated. Thus, during isothermal conditions of the gun barrel 106 the temperatures of the rifling element 302, the gun barrel wall 306, and the gun barrel bore surface 114 will be substantially similar or identical to one another.

Although the example methods, systems, and apparatus described herein may be used to determine average temperatures of the rifling element 302 and the gun barrel wall 306 to reasonably approximate the temperature of the gun barrel bore surface 114, for purposes of clarity the example methods, systems and apparatus are described herein as determining the temperature near the gun barrel bore surface 114. In other words, the temperature near the gun barrel bore surface 114 at the rifled portion 120 can be determined by determining the average temperature of the rifling element 302, which can then be used to reasonably approximate the temperature of the gun barrel bore surface 114 at the rifled portion 120. In a similar manner, the temperature near the gun barrel bore surface 114 at the non-rifled portion 118 can be determined by determining the average temperature of the gun barrel wall 306, which can then be used to reasonably approximate the temperature of the gun barrel bore surface 114 at the non-rifled portion 118.

Now, turning in detail to FIG. 4, the temperature and erosion measurements are made in the rifled portion 120 of the gun barrel 106 based on echoes produced by the shape of the rifling element 302 and the recess 402. Specifically, the echoes are produced by a first land 406 formed by the recess 402 and a second land 408 formed by the rifling element 302. The acoustic transducer 126 may be implemented using an acoustic transducer capable of emitting an acoustic beam having a sufficiently large radius to propagate toward the first and second lands 406 and 408. In this manner, two distinctly detectable echoes may be generated when the acoustic signal (e.g., the acoustic signal 304) is reflected from the first and second lands 406 and 408. An example acoustic transducer having a beam of sufficiently large radius is a 0.25" diameter, 30 MHz ultrasonic transducer. Of course other size transducers may be used depending at least in part on the size and spacing of the lands 406 and 408.

The acoustic transducer 126 may be coupled to the outer surface 112 at a location where the acoustic transducer 126 can emit an acoustic signal (e.g., the acoustic signal 304 of FIG. 3) that will propagate partially toward the first land 406 and partially toward the second land 408. In this manner, when the acoustic transducer 126 emits the acoustic signal 304 into the gun barrel wall 306, a portion of the acoustic signal 304 propagates toward the first land 406 along a direction indicated by arrow 404a, and a portion of the acoustic signal 304 propagates toward the second land 408 along a direction indicated by arrow 404b. As shown in FIG. 4, a recess distance $d_r$ indicates the distance from the outer surface 112 to the first land 406 and a rifling element distance $d_{re}$ indicates the distance from the first land 406 to the second land 408. A first transmit time $t_{t1}$ represents the amount of time required for the acoustic signal 304 to reach the first land 406. A second transmit time $t_{t2}$ represents the amount of time required for the acoustic signal 304 to propagate from the outer surface 112 or the acoustic transducer 126 to the second land 408.

The acoustic signal 304 is reflected from the first and second lands 406 and 408 to produce two distinctly detectable echoes. After the acoustic signal 304 propagates along the direction 404a, it is reflected by the first land 406, which produces a first echo signal that propagates toward the acoustic transducer 126 along a direction generally indicated by arrow 404c. A first echo time $t_{e1}$ represents the amount of time required for the first echo signal to propagate from the first land 406 to the acoustic transducer 126. After the acoustic signal 304 propagates along the direction 404b, it is reflected by the second land 408, which produces a second echo signal that propagates along a direction generally indicated by arrow 404d toward the acoustic transducer 126. A second echo time $t_{e2}$ represents the amount of time required for the second echo signal to propagate from the second land 408 to the acoustic transducer 126.

The temperature and erosion measurements for the rifled portion 120 are determined based on the amount of time required for the acoustic signal 304 to propagate through the rifling element 302. The propagation time (e.g., the transit time) through the rifling element 302 is defined as the amount of time required for the acoustic signal 304 to propagate from the first land 406 to the second land 408 and is denoted herein as a rifling element propagation time $t_{re}$. The distance from the first land 406 to the second land 408 is shown in FIG. 4 as the rifling element thickness $d_{re}$. The rifling element propagation time $t_{re}$ is determined based on a first total propagation time $t_{p1}$ and a second total propagation time $t_{p2}$ as shown in Equation 1 below.

$$t_{re}=t_{p2}-t_{p1}, \text{ where } t_{p1}=t_{t1}+t_{e1} \text{ and } t_{p2}=t_{t2}+t_{e2} \quad \text{Equation 1}$$

As shown above in Equation 1, the first total propagation time $t_{p1}$ is equal to the sum of the times $t_{t1}$ and $t_{e1}$ and the second total propagation time $t_{p2}$ is equal to the sum of the times $t_{t2}$ and $t_{e2}$. The rifling element propagation time $t_{re}$ is equal to the difference between the first and second total propagation times $t_{p1}$ and $t_{p2}$. Although the method of determining the rifling element propagation time $t_{re}$ is shown mathematically in Equation 1 above with respect to transmit time and echo time, an example method that may be used to determine the rifling element propagation time $t_{re}$ may be based on timestamps (e.g., acoustic signal emission timestamps and echo detection timestamps) as described in greater detail below in connection with the example method of FIG. 16.

Figure 5:
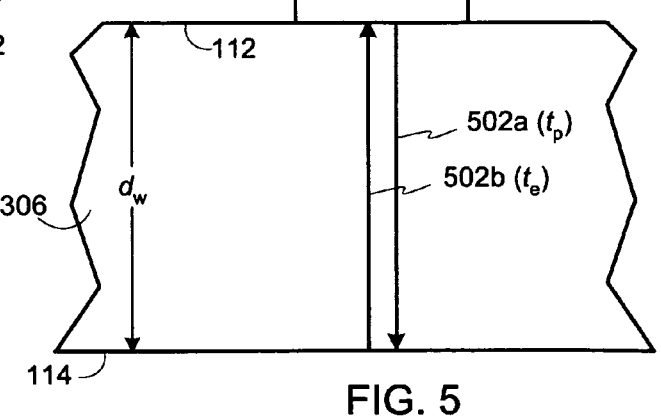
FIG. 5 is a partial view of the gun barrel with the acoustic transducer coupled thereto that is configured to emit acoustic signals in the non-rifled portion of the gun barrel.

FIG. 5 is a partial view of the gun barrel 106 with the acoustic transducer 126 coupled thereto that is configured to emit acoustic signals (e.g., the acoustic signal 304 of FIG. 3) in the non-rifled portion 118 (FIG. 1) of the gun barrel 106. The temperature and erosion measurements are made in the non-rifled portion 118 of the gun barrel 106 based on the amount of time required for the acoustic signal 304 and a corresponding echo to propagate through a wall thickness $d_w$ of the gun barrel wall 306. The wall thickness $d_w$ of a typical gun barrel can vary from 1 to 4 inches. The acoustic transducer 126 emits the acoustic signal 304 into the gun barrel wall 306 (FIG. 3) so that the acoustic signal 304 propagates toward the gun barrel bore surface 114 in a direction generally indicated by arrow 502a. An acoustic signal propagation time $t_p$ represents the amount of time required for the acoustic signal 304 to propagate from the outer surface 112 or the acoustic transducer 126 to the gun barrel bore surface 114. The acoustic signal 304 is then reflected from the gun barrel bore surface 114 to produce an echo. The echo propagates toward the acoustic transducer 126 in a direction generally indicated by arrow 502b. An echo propagation time $t_e$ represents the amount of time required for the echo signal to propagate from the gun barrel bore surface 114 to the acoustic transducer 126.

The temperature and erosion measurements for the non-rifled portion 118 are determined based on the amount of time required for the acoustic signal 304 to propagate through the gun barrel wall 306 (e.g., between the outer surface 112 and the gun barrel bore surface 114). The propagation time through the gun barrel wall 306 is defined as the amount of time required for the acoustic signal 304 to propagate from the outer surface 112 to the gun barrel bore surface 114 and back to the outer surface 112 and is denoted herein as a wall propagation time $t_w$. The wall propagation time $t_w$ is determined based on the signal propagation time $t_p$ and the echo propagation time $t_e$ as shown in Equation 2 below.

$$t_w = t_p + t_e \quad \text{Equation 2}$$

As shown above in Equation 2, the wall propagation time $t_w$ is equal to the sum of the times $t_p$ and $t_e$. Although the method of determining the wall propagation time $t_w$ is shown mathematically in Equation 2 above with respect to the times $t_p$ and $t_e$, an example method that may be used to determine the wall propagation time $t_w$ based on timestamps (e.g., acoustic signal emission timestamps and echo detection timestamps) is described in greater detail below in connection with the example method of FIG. 14.

Figure 6:
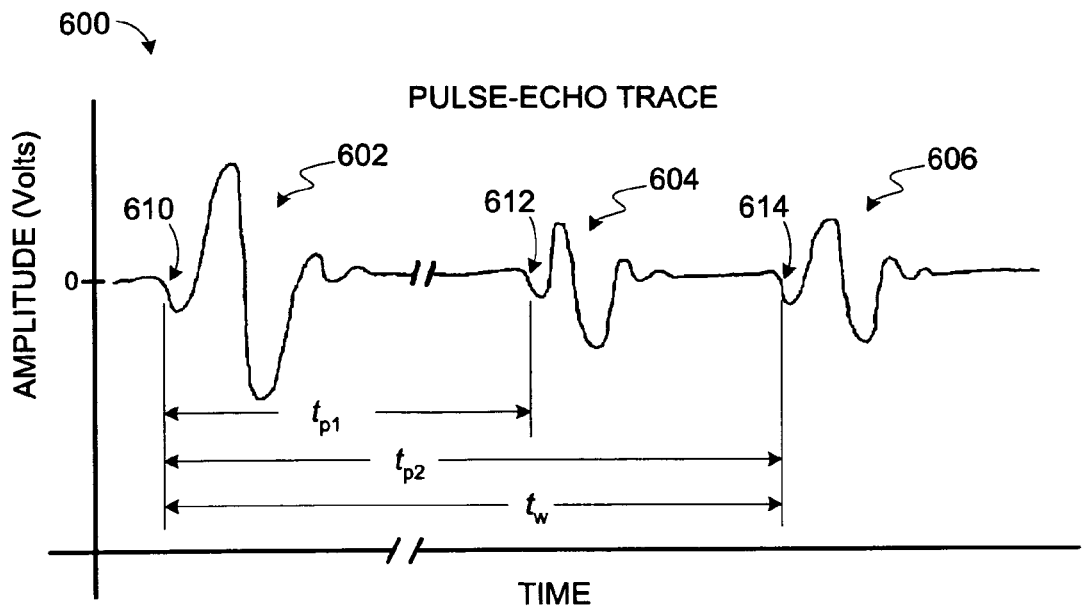
FIG. 6 is a pulse-echo trace showing the time relationship between an acoustic signal emission and corresponding echoes associated with a rifled portion of a gun barrel.

FIG. 6 is a pulse-echo trace 600 showing the time relationship between an acoustic signal emission (e.g., the acoustic signal 304 of FIG. 3) and corresponding first and second echoes associated with the rifled portion 120 of the gun barrel 106. The pulse-echo trace 600 includes an acoustic signal emission waveform 602, a first echo waveform 604, and a second echo waveform 606. The acoustic signal emission waveform 602 may be substantially similar or identical to the waveform of the acoustic signal 304 of FIG. 3. The first and second echo waveforms 604 and 606 may be substantially similar or identical to the first and second echoes described above in connection with FIG. 4 that travel along the directions 404c and 404d.

The acoustic transducers 126 (FIG. 1) may be configured to emit the acoustic signal emission waveform 602 and to detect the first and second echo waveforms 604 and 606. The monitoring system 102 may then determine propagation times based on the emission time of the acoustic signal emission waveform 602 and the detection times of the first and second echo waveforms 604 and 606. Propagation times may be determined using any of a number of known signal processing algorithms. For example, propagation times may be determined by analyzing the waveforms 602, 604, and 606 using peak detection, cross-correlation, matched filter methods, and sweep frequency/inverse filtering methods (e.g., chirp). Of course any other method may be used for determining the propagation times described herein.

The pulse-echo trace 600 represents the times at which the acoustic signal emission waveform 602 is emitted by one or more of the transducers 126 (FIGS. 1, 2, 3, and 4) and the times at which the echo waveforms 604 and 606 are detected by the transducer 126. The first total propagation time $t_{p1}$ of Equation 1 above is equal to an amount of time that lapses between an acoustic signal emission time 610 and a first echo reception time 612. The second total propagation time $t_{p2}$ of Equation 1 above is equal to an amount of time that lapses between the acoustic signal emission time 610 and a second echo reception time 614.

A pulse-echo trace for the non-rifled portion 118 of the gun barrel 106 may be represented using the acoustic signal emission waveform 602 and the second echo waveform 606. However, because the non-rifled portion 118 does not have rifling elements (e.g., the rifling elements 302 of FIGS. 3 and 4), the pulse-echo trace for the non-rifled portion 118 would not have the first echo waveform 604. As shown in FIG. 6 with respect to the waveforms 602 and 606, the wall propagation time $t_w$ of Equation 2 above is equal to an amount of time that lapses between the acoustic signal emission time 610 and the echo reception time 614.

Figure 7:
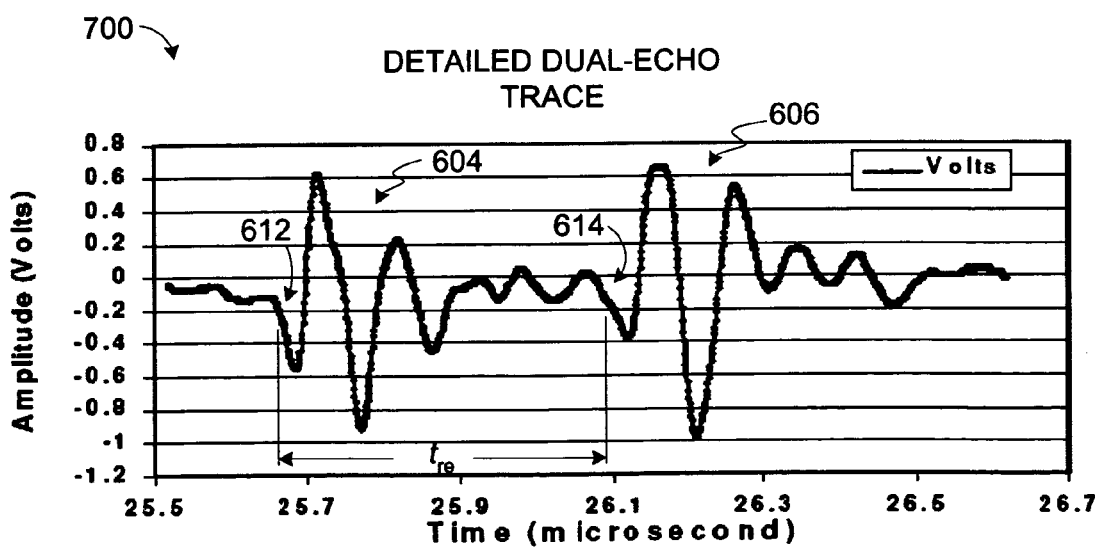
FIG. 7 is a detailed dual-echo trace showing the time relationship between the two acoustic echoes of FIG. 6.

FIG. 7 is a detailed dual-echo trace 700 showing the time relationship between the two acoustic echoes 604 and 606 of FIG. 6. More specifically, the dual-echo trace 700 illustrates the rifling element propagation time $t_{re}$ of Equation 1 above. The rifling element propagation time $t_{re}$ is shown as the amount of time lapsed between reception by one of the acoustic transducers 126 (FIGS. 1, 3, and 4) of the first echo 604 (e.g., the first echo reception time 612) and the reception of the second echo 606 (e.g., the second echo reception time 614).

Figure 8:
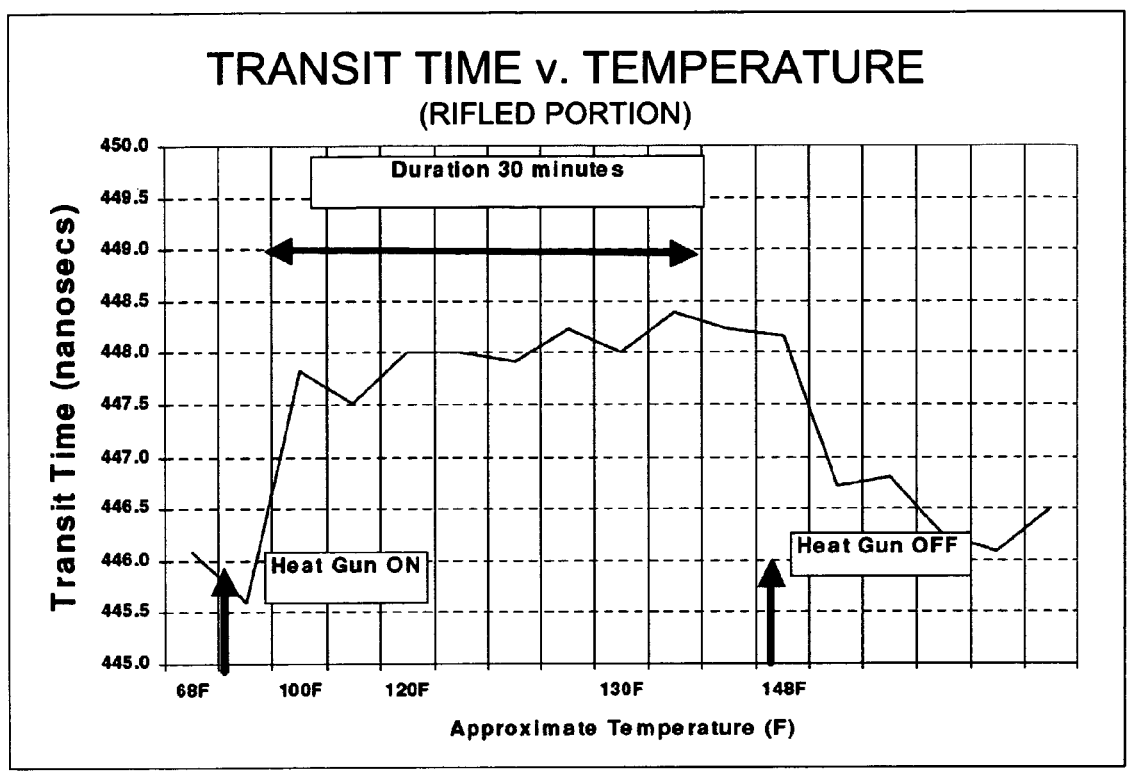
FIG. 8 is a propagation time graph illustrating the relationship between the temperature of a material and the propagation time of acoustic signals emitted into the material.

FIG. 8 is a propagation time graph 800 illustrating the relationship between the temperature of a material and the propagation time of acoustic signals emitted into the material. More specifically, the propagation time graph 800 was generated using the rifling element propagation time $t_{re}$ described above in connection with FIGS. 4 and 7. As shown in the propagation time graph 800, propagation time varies with temperature. More specifically, the rifling element propagation time increases as the temperature increases. The relationship between propagation time and temperature indicates that the temperature of a material may be determined based on the rifling element propagation time $t_{re}$.

The data represented in the propagation time graph 800 was collected in a laboratory by heating a material substantially similar or identical to the material used to make a gun barrel (e.g., the gun barrel 106 of FIGS. 1 and 3), emitting acoustic signals into the material, and measuring the propagation times of the acoustic signals as described above in connection with FIGS. 4-7.

Figure 9:
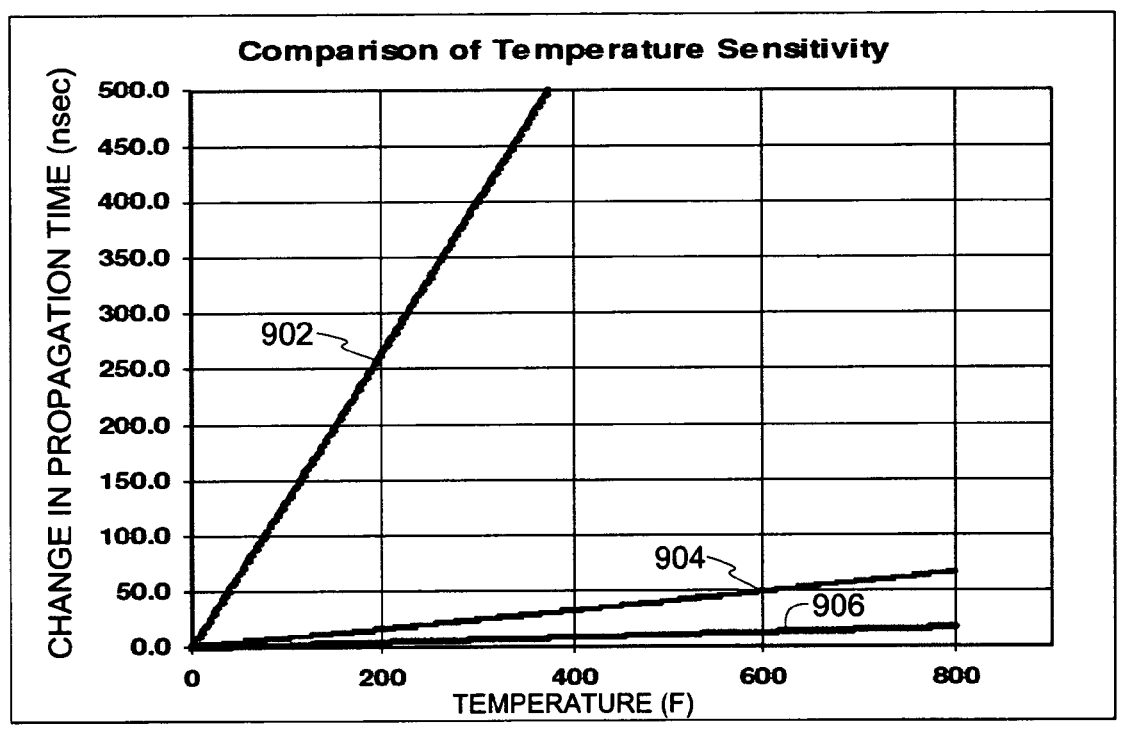
FIG. 9 is an acoustic wave comparison graph that compares the sensitivity of compressional waves and shear waves with respect to the temperature of a material and the propagation time required for a wave to propagate through the material.

FIG. 9 is an acoustic wave comparison graph 900 that compares the sensitivity of compressional waves and shear waves with respect to the temperature of a material and the propagation time required for a wave to propagate through the material. As described above, the example methods, systems, and apparatus described herein may be implemented using compressional waves and/or shear waves. Compressional waves propagate faster through a material, but produce a lower sensitivity when measuring temperature. Shear waves propagate slower through a material and produce a substantially high sensitivity when measuring temperature.

The information plotted in the acoustic wave comparison graph 900 is a plurality of propagation times that change with respect to temperature variation and that are calculated based on a measured acoustic velocity (e.g., a measured speed of sound) and a temperature coefficient of velocity change $y_f$ (described below in connection with FIGS. 10 and 11) of the non-rifled portion 118 and the rifled portion 120 of the gun barrel 106. A non-rifled section compressional wave line 902 is generated by collecting propagation time data based on compressional waves emitted into a gun barrel wall (e.g., the gun barrel wall 306 of FIG. 3) of a non-rifled portion (e.g., the non-rifled portion 118) of a typical 5" caliber gun barrel wall. A rifled section shear wave line 904 is generated by collecting propagation time data based on shear waves emitted into a rifled portion (e.g., the rifled portion 120) of a typical 5" caliber gun barrel wall. A rifled section compression wave line 906 is generated by collecting propagation time data based on compressional waves emitted into a rifled portion of a typical 5" caliber gun barrel wall.

The non-rifled section compressional wave line 902, which indicates a greater degree of sensitivity than the rifled section lines 904 and 906, is generated by measuring the propagation time of a compressional wave as it propagates through the gun barrel wall thickness $d_w$ (FIG. 4) while the rifled section lines 904 and 906 are generated by measuring propagation times of acoustic waves through the rifling element thickness $d_{re}$ (FIG. 5). A short propagation distance of 0.050" associated with the rifling elements 302 is one reason for the difference in sensitivities between the non-rifled section shear wave line 902 and the rifled section lines 904 and 906 illustrated in the acoustic wave comparison graph 900. Although the propagation time sensitivity in the rifled portion is substantially less than the propagation time sensitivity in the non-rifled portion, measuring the double echo in the rifled section results in a highly localized temperature measurement because the propagation time measured in the rifled portion is based on the rifling element thickness $d_{re}$.

Figure 10:
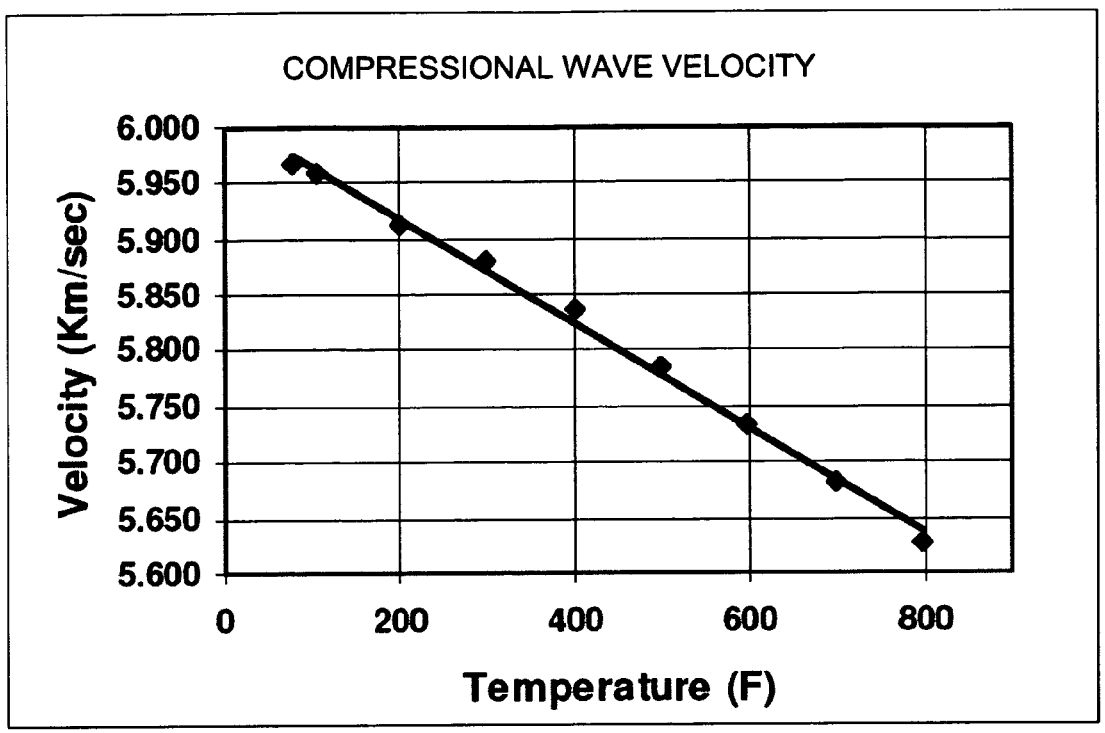
FIG. 10 is a graph that may be used to determine the temperature coefficient of velocity change for a material based on the propagation speed of compressional waves through the material as a function of temperature.
Figure 11:
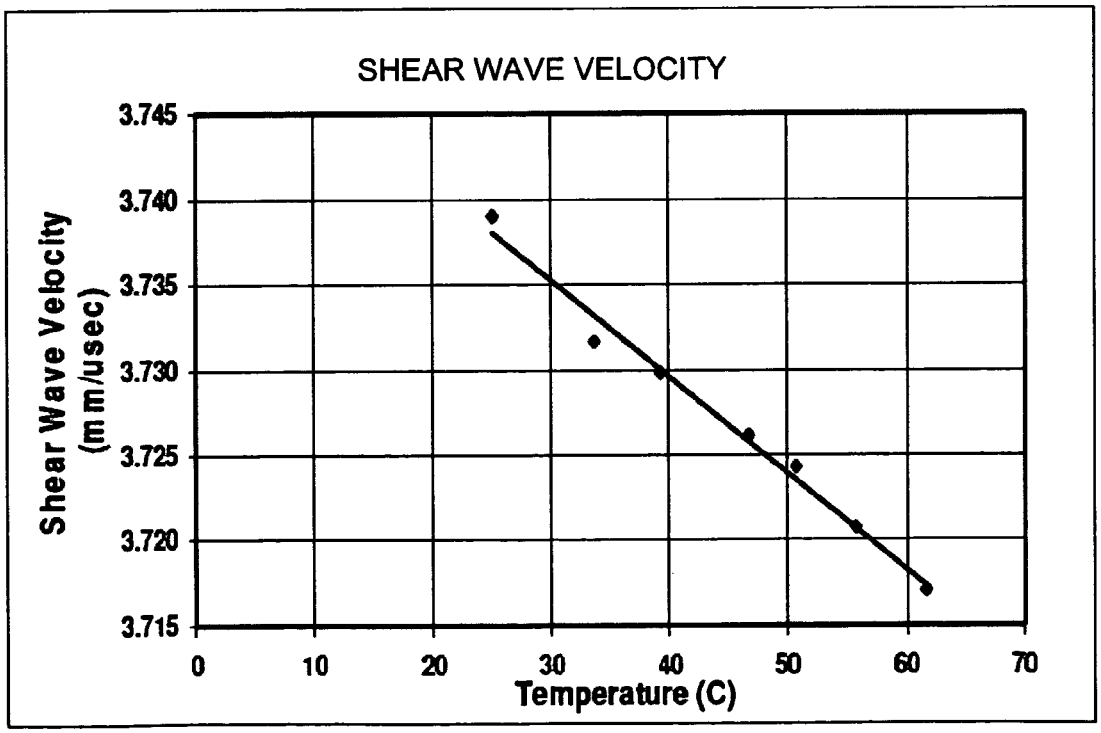
FIG. 11 is a graph that may be used to determine the temperature coefficient of velocity change for a material based on the propagation speed of shear waves through the material as a function of temperature.

FIGS. 10 and 11 are graphs that may be used to determine the temperature coefficient of velocity change $y_f$ for a material based on the propagation speed of acoustic waves through the material as a function of temperature. The graph of FIG. 10 may be used to determine the temperature coefficient of velocity change $y_f$ for compressional waves (i.e., longitudinal waves, P-waves) and the graph of FIG. 11 may be used to determine the temperature coefficient of velocity change $y_f$ for shear waves (i.e., transverse waves, S-waves). The temperature coefficient of velocity change $y_f$ quantifies the change in the propagation speed of ultrasonic waves through a material as the temperature of the material changes. As shown in FIGS. 10 and 11, for both compressional waves and shear waves, the speed of acoustic waves through a material decreases as the temperature of the material increases.

The temperature coefficient of velocity change $y_f$ is a predetermined value that varies from one material to another. The data points that form the lines 802 and 902 of FIGS. 10 and 11, respectively, may be collected in a laboratory environment for a desired material. For instance, the data shown in the graphs of FIGS. 10 and 11 may be generated by obtaining a piece of a material used to manufacture a gun barrel or by obtaining a section of a gun barrel, heating the material, and measuring the velocity of acoustic waves through the material. The temperature coefficient of velocity change $y_f$ may be determined for any type of material in this manner.

As described below, the temperature coefficient of velocity change $y_f$ is used in combination with the propagation times described above in connection with FIGS. 4-6 to determine the temperature near the gun barrel bore surface 114 and the erosion of the gun barrel bore surface 114. The temperature and erosion of the non-rifled portion 118 and rifled portion 120 of the gun barrel 106 may be determined based on mathematical operations described in detail below and the propagation times (e.g., the times $t_{p1}$, $t_{p2}$, $t_w$, $t_{re}$, etc.) and temperature coefficient of velocity change $y_f$ described above. The mathematical relationship between propagation time of an acoustic signal (e.g., the acoustic signal 304 of FIG. 3) and an isothermal temperature is shown below in Equation 3a. For a non-isothermal temperature, the relationship between propagation time (i.e., propagation time) of an acoustic signal (e.g., the acoustic signal 304 of FIG. 3) and the non-isothermal temperature is shown below in Equation 3b.

$$t(T) = \frac{2 \cdot d}{V(T_C)} \cdot \frac{1}{(1 + y_f(T - T_C))} \qquad \text{Equation 3a}$$

-continued $$t(T) = \int_0^d \frac{1}{V(T, x)} dx \approx \frac{2 \cdot d}{V(T_C)} \cdot \frac{1}{(1 + y_f(T - T_C))} \qquad \text{Equation 3b}$$

As shown in Equations 3a and 3b above, the propagation time at a monitored temperature t(T) (i.e., a monitored propagation time t(T)) may be determined based on the monitored temperature T, a calibration temperature $T_C$, the temperature coefficient of velocity change $y_f$, a propagation distance d, and a speed of sound at the calibration temperature $V(T_C)$ (i.e., a calibration temperature speed of sound $V(T_C)$).

Equation 3a may be used to determine a monitored propagation time t(T) during isothermal conditions of a material and Equation 3b may be used to determine a monitored propagation time t(T) during non-isothermal conditions of a material. Specifically, as shown above, Equation 3b indicates that during a non-isothermal condition, the monitored propagation time t(T) is equal to an average temperature determined using an integral over a distance d (e.g., the rifling element thickness $d_{re}$, the gun barrel wall thickness $d_w$, etc.). In this manner, the integral of Equation 3b may be used to determine an average temperature when thermal gradients are present in the gun barrel 106. Further, as shown above in Equation 3b, the monitored propagation time t(T) of Equation 3a may be reasonably approximated using the integral of Equation 3b.

The calibration temperature $T_C$ is a temperature at which the temperature and erosion monitoring system 102 is calibrated. The propagation distance d is the distance through which the propagation time of an acoustic signal (e.g., the acoustic signal 304 of FIG. 3) is measured. For example, in the non-rifled portion 118 of the gun barrel 106, the propagation distance d is equal to the thickness $d_w$ of the gun barrel wall 306 (e.g., the distance from the outer surface 112 to the gun barrel bore surface 114). In the rifled portion 118 of the gun barrel 106, the propagation distance d is equal to the thickness $d_{re}$ of the rifled element 302. Although, Equation 3a is generally applicable to determining a monitored propagation time in the non-rifled and rifled portions 118 and 120, applicability of Equation 3a to the rifled portion 120 is described in greater detail below in connection with Equations 7-11.

The calibration temperature speed of sound $V(T_C)$ is the speed of an acoustic signal (e.g., the acoustic signal 304) as it travels through a material having a temperature that is measured as the calibration temperature $T_C$ or that is substantially equal to the calibration temperature $T_C$. The calibration temperature speed of sound $V(T_C)$ may be determined by measuring the propagation time of an acoustic signal as it propagates through a material having a known thickness and the calibration temperature $T_C$. As described below, the temperature and erosion of the gun barrel 106 may be determined independent of knowing the calibration temperature speed of sound $V(T_C)$ or the initial material thickness (i.e., an initial propagation distance).

As shown above in Equation 3a, the calibration temperature $T_C$ is subtracted from the monitored temperature T to determine a temperature difference value $(T-T_C)$. The temperature difference value $(T-T_C)$ is then multiplied by the temperature coefficient of velocity change $y_f$ to determine a product value $(y_f(T-T_C))$. The product value $(y_f(T-T_C))$ is then added to one to determine a sum value $(1+y_f(T-T_C))$. The propagation distance value d is then multiplied by two to determine a second product value $(2 \cdot d)$ and the second product value $(2 \cdot d)$ is divided by the calibration temperature speed of sound $V(T_C)$ to determine a quotient value $$\frac{2 \cdot d}{V(T_C)}.$$

An inverse of the sum value $$\frac{1}{(1 + y_f(T - T_C))}$$

is then multiplied by the quotient value $$\frac{2 \cdot d}{V(T_C)}$$

to determine the monitored propagation time t(T).

To determine temperature and erosion independent of knowing the calibration temperature speed of sound $V(T_C)$ or the initial material thickness (i.e., initial propagation distance), the temperature and erosion monitoring system 102 (FIGS. 1 and 2) is calibrated while the gun barrel 106 is in an isothermal condition. More specifically, the calibration temperature $T_C$ is determined by measuring the temperature of the gun barrel 106 using, for example, the temperature transducer 124 when the gun barrel 106 is in an isothermal condition. The temperature and erosion monitoring system 102 is then used to emit acoustic signals into the gun barrel wall 306 (FIG. 3) and measure the propagation time of the acoustic signals to determine a propagation time at calibration temperature value $t(T_C)$ (i.e., the calibration propagation time $t(T_C)$). The relationship between the calibration propagation time $t(T_C)$, the propagation distance d, and the calibration temperature speed of sound $V(T_C)$ is expressed in mathematical terms as shown below in Equation 4.

$$t(T_C) = \frac{2 \cdot d}{V(T_C)} \qquad \text{Equation 4}$$

As shown in Equation 4 above, the calibration propagation time $t(T_C)$ is determined by multiplying the propagation distance d by two to determine a product value $2 \cdot d$ and dividing the product value $2 \cdot d$ by the calibration temperature speed of sound $V(T_C)$. The example methods described below in connection with FIG. 13 may be used to calibrate the temperature and erosion monitoring system 102 (FIGS. 1 and 2) by determining the calibration propagation time $t(T_C)$ of Equation 4 above for the non-rifled portion 118 of the gun barrel 106.

By calibrating the temperature and erosion monitoring system 102 (FIGS. 1 and 2) at the calibration temperature $T_C$ and determining the calibration propagation time $t(T_C)$ as shown in Equation 4 above, the monitored propagation time t(T) may be determined independent of knowing the calibration temperature speed of sound $V(T_C)$ or the material thickness d. The relationship between the calibration propagation time $t(T_C)$ and the monitored propagation time t(T) is shown in Equation 5 below.

$$t(T) = \frac{t(T_C)}{(1 + y_f(T - T_C))} \quad \text{Equation 5}$$

As shown in Equation 5 above, the monitored propagation time t(T) may be determined independent of having a known material thickness d and a calibration temperature speed of sound V(T$_C$). The monitored propagation time t(T), as shown above in Equation 5, is determined by dividing the calibration propagation time t(T$_C$) by the sum value (1+y$_f$(T−T$_C$)).

The temperature near the gun barrel bore surface 114 in the non-rifled portion 118 of the gun barrel 106 may be determined based on the monitored propagation time t(T) and the calibration propagation time t(T$_C$) as shown in Equation 6 below.

$$T = T_C + \frac{(t(T_C) - t(T))}{(y_f \cdot t(T))} \quad \text{Equation 6}$$

As shown in Equation 6 above, the monitored propagation time t(T) is subtracted from the calibration propagation time t(T$_C$) to determine a difference value (t(T$_C$)−t(T)). The temperature coefficient of velocity change y$_f$ is then multiplied by the monitored propagation time t(T) to determine a product value (y$_f$·t(T)). The monitored temperature T near the gun barrel bore surface 114 is then determined by dividing the difference value (t(T$_C$)−t(T)) by the product value (y$_f$·t(T)). The example methods described below in connection with FIG. 17 may be used to determine the temperature near the gun barrel bore surface 114 in the non-rifled portion 118 of the gun barrel 106 based on Equation 6 above.

The temperature near the gun barrel bore surface 114 and the erosion of the gun barrel bore surface 114 may be monitored based on the rifling element propagation time t$_{re}$ described above in connection with FIGS. 4, 6, and 7. The rifling element propagation time t$_{re}$ is determined based on the first total propagation time t$_{p1}$ and the second total propagation time t$_{p2}$ described above in connection with FIGS. 4 and 6. The first total propagation time t$_{p1}$ at the monitored temperature T is expressed below as the first total monitored propagation time t$_{p1}$(T) in Equation 7. The second total propagation time t$_{p2}$ at the monitored temperature T is expressed below as the second total monitored propagation time t$_{p2}$(T) in Equation 8. Equation 9 below shows the relationship between a rifling element monitored propagation time t$_{re}$(T) and the first and second total monitored propagation times at the monitored temperature t$_{p1}$(T) and t$_{p2}$(T).

$$t_{p1}(T) = \frac{2 \cdot d_w}{V(T_C)} \cdot \frac{t(T_C)}{(1 + y_f(T - T_C))} \quad \text{Equation 7}$$

$$t_{p2}(T) = t_{p1}(T) - t_{re}(T), \text{ where} \quad \text{Equation 8}$$

$$t_{re}(T) = \frac{2 \cdot d_{re}}{V(T_C)} \cdot \frac{t(T_C)}{(1 + y_f(T - T_C))}$$

$$t_{re}(T) = t_{p1}(T) - t_{p2}(T) \quad \text{Equation 9}$$

Equation 7 above is substantially similar or identical to Equation 3a above because the first total monitored propagation time t$_{p1}$(T) measures the propagation time required for an acoustic signal to propagate through the gun barrel wall thickness d$_w$ (FIG. 4). Equation 8 shows the relationship between the first total monitored propagation time t$_{p1}$(T), the rifling element thickness d$_{re}$, and the second total monitored propagation time t$_{p2}$(T). More specifically, the second total monitored propagation time t$_{p2}$(T) is equal to the difference between the first total monitored propagation time t$_{p1}$(T) and the rifling element monitored propagation time t$_{re}$(T). Equation 9 shows that the rifling element monitored propagation time t$_{re}$(T) is determined by subtracting the second total monitored propagation time t$_{p2}$(T) from the first total monitored propagation time t$_{p1}$(T).

The rifling element monitored propagation time t$_{re}$(T) may be determined independent of knowing the calibration temperature speed of sound V(T$_C$) by calibrating the temperature and erosion monitoring system 102 (FIGS. 1 and 2) at the rifled portion 120 of the gun barrel 106 when the gun barrel 106 is at the calibration temperature T$_C$. The relationship between the rifling calibration element propagation time t$_{re}$(T$_C$) and the calibration temperature speed of sound V(T$_C$) is shown in Equation 10 below.

$$t_{re}(T_C) = \frac{2 \cdot d_{re}}{V(T_C)} \quad \text{Equation 10}$$

As shown in Equation 10 above, the rifling element calibration propagation time t$_{re}$(T$_C$) is equal to two multiplied by the rifling element thickness d$_{re}$ and divided by the calibration temperature speed of sound V(T$_C$).

The temperature near the gun barrel bore surface 114 in the rifled portion 120 of the gun barrel 106 may be determined based on the rifling element monitored propagation time t$_{re}$(T) and the rifling element calibration propagation time t$_{re}$(T$_C$) as shown in Equation 11 below.

$$T_{re} = T_C + \frac{(t_{re}(T_C) - t_{re}(T))}{(y_f \cdot t_{re}(T))} \quad \text{Equation 11}$$

Equation 11 is similar to Equation 6. However, as shown above, Equation 11 may be used to determine the temperature T$_{re}$ near the gun barrel bore surface 114 in the rifled portion 120 of the gun barrel 106 based on the rifling element monitored propagation time t$_{re}$(T). As shown in Equation 11 above, the rifling element monitored propagation time t$_{re}$(T) is subtracted from the rifling element calibration propagation time t$_{re}$(T$_C$) to determine a difference value (t$_{re}$(T$_C$)−t$_{re}$(T)). The temperature coefficient of velocity change y$_f$ is then multiplied by the rifling element monitored propagation time t$_{re}$(T) to determine a product value (y$_f$·t$_{re}$(T)). The difference value (t$_{re}$(T$_C$)−t$_{re}$(T)) is then divided by the product value (y$_f$·t$_{re}$(T)) to determine a quotient value $$\frac{(t_{re}(T_C) - t_{re}(T))}{(y_f \cdot t_{re}(T))}.$$

The rifling element monitored temperature T$_{re}$ near the gun barrel bore surface 114 at the rifled portion 120 is then determined by adding the quotient value $$\frac{(t_{re}(T_C) - t_{re}(T))}{(y_f \cdot t_{re}(T))}$$

to the calibration temperature $T_C$. The example methods described below in connection with FIG. 18 may be used to determine the temperature $T_{re}$ near the gun barrel bore surface 114 in the rifled portion 120 of the gun barrel 106 based on Equation 11 above.

During firing regiments, gun barrels may often heat up to 800° F. causing thermal expansion of the gun barrels (e.g., the gun barrel wall 306 of FIG. 3). The thermal expansion of the gun barrel bore 106 may be quantified to increase the accuracy of the temperature measured near the gun barrel bore surface 114. An increase in material temperature typically causes a material to expand and, thus, causes an increase in propagation distance, which in turn may affect the amount of time required for an acoustic signal to propagate through the material. As described below, thermal expansion may affect temperature measurements in both the non-rifled portion 118 of the gun barrel 106 and the rifled portion 120 of the gun barrel 106.

Thermal expansion of the gun barrel wall 306 (FIG. 3) may have a substantially significant effect on determining temperatures of the gun barrel 106 near the gun barrel bore surface 114. For example, thermal expansion tests of the gun barrel wall 306 at the non-rifled portion 118 of the gun barrel 106 indicate that thickness changes of the gun barrel wall 306 following a firing regiment may vary from 0.003" (after firing 24 rounds of NACO and 18 rounds of ERGM over 141 minutes) to 0.009" (after firing 500 AVG MK 67 (NACO) rounds at 2 rounds per minute in an EX MOD 4 GUN). A wall thickness change of 0.003" in the non-rifled portion 118 of the gun barrel 106 may generate a temperature underestimation of 18° F.

A thermal expansion coefficient EB may be used to include the effects of thermal expansion when determining a temperature near the gun barrel bore surface 114 as described herein. The thermal expansion coefficient EB quantifies the effects of temperature on the amount of expansion of a material. The value of the thermal expansion coefficient EB is different for each material type and may be obtained from thermal modeling of a particular material type or from a material properties and standards reference publication. The effects of thermal expansion on the temperature measurements described herein may be substantially eliminated or may be made substantially negligible by determining the propagation distance or thickness of a material (e.g., the gun barrel wall thickness $d_w$) during elevated temperatures based on Equation 12 below.

$$d_E = d_o \cdot (1 + EB \cdot (T - T_C)) \quad \text{Equation 12}$$

As shown above in Equation 12, an expanded material thickness $d_E$ may be determined based on an initial material thickness $d_o$, the thermal expansion coefficient EB, the monitored temperature T, and the calibration temperature $T_C$. The expanded material thickness $d_E$ represents the distance through which an acoustic signal (e.g., the acoustic signal 304 of FIG. 3) propagates when it is emitted into a material (e.g., the gun barrel wall 306) at elevated temperatures. During conditions of elevated temperatures such as during or following a firing regiment, the gun barrel wall thickness $d_w$ may be determined based on Equation 12 above, where the gun barrel wall thickness $d_w$ is set equal to the expanded material thickness $d_E$. The initial thickness $d_o$ is a known distance or known thickness of a material through which an acoustic signal propagates when calibrating the monitoring system 102. For example, if the monitoring system 102 performs a calibration for the non-rifled portion 118 of the gun barrel 106, the initial thickness $d_o$ is set equal to a known thickness of the gun barrel wall 306 (FIG. 3) (e.g., a known thickness of the gun barrel wall thickness $d_w$). If the monitoring system 102 performs a calibration for the rifled portion 120 of the gun barrel 106, the initial thickness do is set equal to a known thickness of one of the rifling elements 302 (FIG. 3) (e.g., a known thickness of the rifling element thickness $d_{re}$).

As shown above in Equation 12, the expanded material thickness $d_E$ may be determined by first subtracting the calibration temperature $T_C$ from the monitored temperature T to determine a difference value $(T-T_C)$. The difference value $(T-T_C)$ is then multiplied by the thermal expansion coefficient EB to determine a product value $(EB \cdot (T-T_C))$. The product value $(EB \cdot (T-T_C))$ is then added to one to determine a sum value $(1+EB \cdot (T-T_C))$. The expanded material thickness $d_E$ is then determined by multiplying the sum value $(1+EB \cdot (T-T_C))$ and the initial material thickness $d_o$.

A material expansion compensated monitored temperature $T_E$ of the gun barrel 106 near the gun barrel bore surface 114 (FIGS. 1, 3, and 5) may be determined during or subsequent to a firing regiment using the thermal expansion coefficient EB as shown below in Equation 13, 14, and 15.

$$t(T_C) = \frac{2 \cdot d_O}{V(T_C)} \quad \text{Equation 13}$$

$$t(T) = \frac{2 \cdot d_O \cdot (1 + EB \cdot (T - T_C))}{V(T_C)} \cdot \frac{1}{(1 + y_f(T - T_C))} \quad \text{Equation 14}$$

$$T_E = T_C + \frac{(t(T_C) - t(T))}{(y_f \cdot t(T) - EB \cdot t(T))} \quad \text{Equation 15}$$

An expansion compensated monitored temperature $T_E$ may be determined by obtaining a calibration propagation time $t(T_C)$ during a system calibration routine. As shown above in Equation 13, the calibration propagation time $t(T_C)$ is based on an initial thickness $d_o$ and the calibration temperature speed of sound $V(T_C)$.

As shown above in Equation 14, a monitored propagation time $t(T)$ obtained during a thermal expansion condition of the gun barrel 106 is directly proportional to the initial thickness $d_o$ and the thermal expansion coefficient EB, and is inversely proportion to the calibration temperature speed of sound $V(T_C)$. Equations 13 and 14 may be used to form Equation 15 to determine the expansion compensated monitored temperature $T_E$.

As shown above in Equation 15, the monitored propagation time $t(T)$ is multiplied by the thermal expansion coefficient EB to determine a first product value $(EB \cdot t(T))$. The monitored propagation time $t(T)$ is multiplied by the temperature coefficient of velocity change $y_f$ to determine a second product value $(y_f t(T))$. The monitored propagation time $t(T)$ is subtracted from the calibrated propagation time $t(T_C)$ to determine a first difference value $(t(T_C)-t(T))$. The first product value $(EB \cdot t(T))$ is subtracted from the second product value $(y_f t(T))$ to determine a second difference value $(y_f t(T)-EB \cdot t(T))$. The first difference value $(t(T_C)-t(T))$ is then divided by the second difference value $(y_f t(T)-EB \cdot t(T))$ to determine a quotient value $$\frac{(t(T_C) - t(T))}{(y_f \cdot t(T) - EB \cdot t(T))}.$$

The thermal expansion compensated monitored temperature $T_E$ is then determined by adding the quotient value $$\frac{(t(T_C) - t(T))}{(y_f \cdot t(T) - EB \cdot t(T))}$$

to the calibration temperature $T_C$.

Equation 15 may be used to determine the expansion compensated monitored temperature $T_E$ for the non-rifled portion 118 and the rifled portion 120 of the gun barrel 106. However, for the rifled portion 120 of the gun barrel 106, the calibration propagation time $t(T_C)$ may be replaced with the rifling element calibration propagation time $t_{re}(T_C)$ and the monitored propagation time $t(T)$ may be replaced with the rifling element monitored propagation time $t_{re}(T)$.

Thermal expansion effects on material thickness (e.g., propagation distance) and temperature effects on the speed of sound produce additive effects on the propagation time of an acoustic wave through a material. For example, as the temperature of the gun barrel 106 increases, the gun barrel wall thickness $d_w$ increases due to thermal expansion, thus increasing the propagation time of an acoustic wave. Additionally, the increased temperature in the gun barrel 106 decreases the speed of sound, which also increases the propagation time of the acoustic wave. However, these effects can be quantified through calibrations using the temperature coefficient of velocity change $y_f$ and the thermal expansion coefficient EB, which may then be used to determine temperature as shown above in Equation. 15.

For a typical gun barrel material (e.g., a steel material), the temperature coefficient of velocity change $y_f$ is generally negative and often ranges from −100 to −175 parts per million per degree centigrade. The thermal expansion coefficient EB is generally positive and ranges from 5 to 15 parts per million per degree centigrade. Thus, thermal expansion increases the magnitude of the denominator of Equation 15 (e.g., the second difference value $(y_f \cdot t(T) - EB \cdot t(T))$) by 5 to 15 percent for both the non-rifled portion 118 and the rifled portion 120.

The erosion of the gun barrel bore surface 114 (FIGS. 1 and 3-5) in the non-rifled portion 118 (FIG. 1) and the rifled portion 120 (FIG. 1) of the gun barrel 106 (FIG. 1) may be determined based on propagation time measurements taken during isothermal conditions of the gun barrel 106. More specifically, erosion occurs slowly over time after many thermal cycles or firings of the gun 104 (FIG. 1). As described above, the propagation time is a function of material thickness (e.g., the propagation distance) and acoustic or sound velocity $V(T)$. Therefore, as the gun barrel bore surface 114 erodes, the gun barrel wall thickness $d_w$ and/or the rifling element thickness $d_{re}$ decrease, and the propagation time of an acoustic signal emitted into the gun barrel wall 306 decreases.

The amount of erosion of the gun barrel bore surface 114 may be determined by measuring the propagation time of an acoustic wave emitted into the gun barrel wall 306 when the gun barrel 106 is at a known temperature such as, for example, the calibration temperature $T_C$. As described above, the calibration temperature $T_C$ may be determined using a thermocouple (e.g., the temperature transducer 124 of FIGS. 1 and 2) engaged to the outer surface 112 (FIGS. 1, 3, 4, and 5) of the gun barrel 106. After a firing regiment, the temperature and erosion monitoring system 102 may monitor the temperature of the outer surface 112 of the gun barrel 106 via the temperature transducer 124 to determine when the gun barrel 106 has cooled off and/or reached an isothermal condition. When the gun barrel 106 reaches an isothermal condition, the temperature and erosion monitoring system 102 may measure the propagation time of an acoustic signal emitted into the gun barrel wall 306. The temperature and erosion monitoring system 102 may measure the propagation times of acoustic signals in this manner after several firing regiments and, at some subsequent time, analyze the propagation times measured during the isothermal conditions to determine the amount of erosion that has occurred in the gun barrel bore surface 114.

An amount of erosion ("$\epsilon$") may be determined based on Equation 16 and 17 below.

$$t(T_C, \epsilon) = \frac{2 \cdot (d - \epsilon)}{V(T_C)} \qquad \text{Equation 16}$$

$$\epsilon = \frac{V(T_C) \cdot (t(T_C, 0) - t(T_C, \epsilon))}{2} \qquad \text{Equation 17}$$

As shown in Equation 16 above, the propagation time as a function of the calibration temperature and the amount of erosion $t(T_C, \epsilon)$ is determined based on the propagation distance d, the amount of erosion $\epsilon$, and the calibration temperature speed of sound $V(T_C)$. The propagation distance d may be set equal to an initial thickness or known thickness such as, for example, the initial thickness $d_o$ described above in connection with Equation 12. For example, for the non-rifled portion 118 of the gun barrel 106, the propagation distance d may be set equal to a known or initial thickness value of the gun barrel wall thickness $d_w$. For the rifled portion 120 of the gun barrel 106, the propagation distance d may be set equal to a known or initial thickness value of the rifling element thickness $d_{re}$. For the non-rifled portion 118, the amount of erosion $\epsilon$ corresponds to the amount of erosion on the non-rifled surface of the gun barrel bore surface 114 at the non-rifled portion 118. For the rifled portion 120, the amount of erosion $\epsilon$ corresponds to the amount of erosion of the rifling elements 302 (FIG. 3).

As shown in Equation 16 above, the propagation time as a function of the calibration temperature and the amount of erosion $t(T_C, \epsilon)$ is determined by subtracting the amount of erosion $\epsilon$ from the propagation distance d to determine a difference value $(d-\epsilon)$, multiplying the difference value $(d-\epsilon)$ by two to determine a product value $2 \cdot (d-\epsilon)$, and dividing the product value $2(d-\epsilon)$ by the calibration temperature speed of sound $V(T_C)$.

Equation 17 may be generated based on Equation 16 and Equation 13, and may be used to determine the amount of erosion $\epsilon$. As shown in Equation 17, the propagation time as a function of calibration temperature and erosion $t(T_C, \epsilon)$ is subtracted from the calibration propagation time $t(T_C, 0)$ to determine a difference value $(t(T_C,0)-t(T_C,\epsilon))$. The difference value $(t(T_C,0)-t(T_C,\epsilon))$ is then multiplied by the calibration temperature speed of sound $V(T_C)$ to produce a product value $V(T_C) \cdot (t(T_C,0)-t(T_C,\epsilon))$. The amount of erosion $\epsilon$ is then determined by dividing the product value $V(T_C) \cdot (t(T_C,0)-t(T_C,\epsilon))$ by two.

FIGS. 12 through 20 are flow diagrams that depict example methods associated with monitoring temperature and erosion of a gun barrel (e.g., the gun barrel 106 of FIGS. 1 and 3). The example methods depicted in the flow diagrams of FIGS. 12 through 20 may be implemented in software, hardware, and/or any combination thereof. For example, the example methods may be implemented in software that is executed on the temperature and erosion monitoring system 102 of FIGS. 1 and 2 and/or the central processing system 206 of FIG. 2. Although the example methods are described below as a particular sequence of operations, one or more operations may be rearranged, added, and/or removed to achieve the same or similar results.

Figure 12:
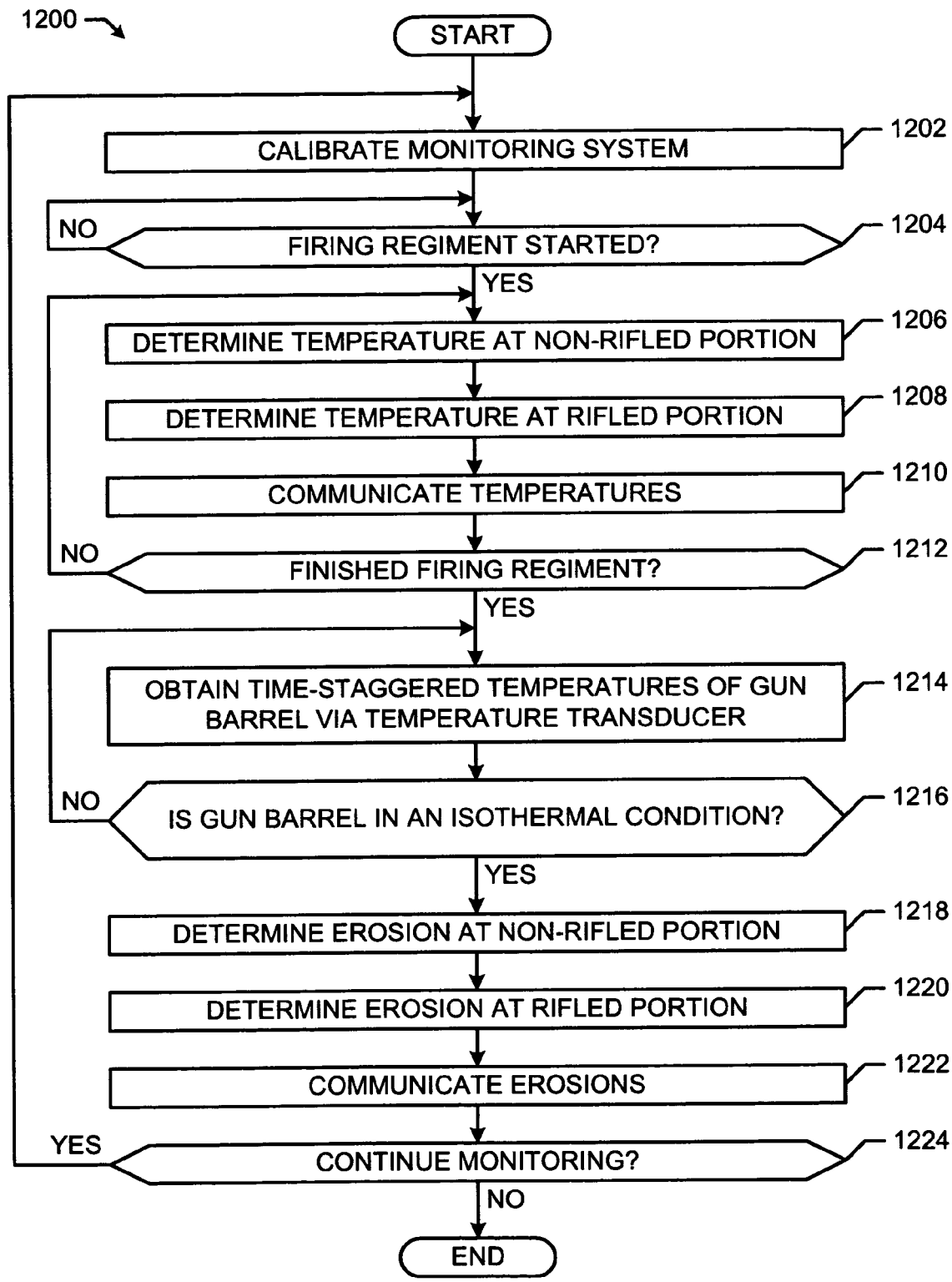
FIG. 12 is a flow diagram of an example method that may be used to monitor the temperature and erosion of a gun barrel.

FIG. 12 is a flow diagram of an example method that may be used to monitor the temperature and erosion of the gun barrel 106 (FIGS. 1 and 3). More generally, the example method of FIG. 12 may be used to monitor temperature and erosion of an elongated member (e.g., the gun barrel 106, a tubular structure, etc.) having a cavity (e.g., the gun barrel bore 106 of FIG. 1, a passage, etc.) therein. Although the example method of FIG. 12 may be implemented using a combination of the example temperature and erosion monitoring system 102 of FIGS. 1 and 2 and the central processing system 206 of FIG. 2, the example method is described below as being implemented using the example temperature and erosion monitoring system 102.

Initially, the temperature and erosion monitoring system 102 is calibrated (block 1202). The monitoring system 102 is calibrated based on the calibration temperature $T_C$ described above to determine the calibration propagation time $t(T_C)$ of an acoustic signal emitted into the gun barrel wall 306 (FIG. 3). The monitoring system 102 is calibrated for the non-rifled and rifled portions 118 and 120 of the gun barrel 106 as described in greater detail below in connection with FIGS. 13-16.

The monitoring system 102 then determines if the gun 104 has started a firing regiment (block 1204). More specifically, the monitoring system 102 determines if one or more rounds have been fired by the gun 104 to determine whether to begin monitoring the temperature near the gun barrel bore surface 114. The monitoring system 102 may determine if one or more rounds have been fired using any one or more of several techniques. For example, the central processing system 206 may be integrated with the firing controls of the gun 104 so that when the gun 104 fires a round, the central processing system 206 can notify the monitoring system 102 when one or more rounds are fired. Alternately, a vibration sensor may be used to detect a firing status of the gun 104. For example, the vibration sensor may be communicatively coupled to the monitoring system 102 and mechanically coupled to the gun 104 and configured to detect recoil motions associated with a firing regiment. An example implementation may include a transducer (e.g., one of the transducers 126 of FIGS. 1 and 2) with an integral vibration sensor. If the monitoring system 102 determines at block 1204 that a firing regiment has not started, the monitoring system 102 repeats the operation of block 1204 to continue monitoring the firing status of the gun 104.

If the monitoring system 102 determines at block 1204 that a firing regiment has started, then the monitoring system 102 determines the temperature T near the gun barrel bore surface 114 at the non-rifled portion 118 of the gun barrel 106 (FIG. 1) (block 1206). The monitoring system 102 may determine the temperature near the gun barrel bore surface 114 in the non-rifled portion 118 based on Equation 6 above and the example method described in detail below in connection with FIG. 17.

The monitoring system 102 may then determine the temperature $T_{re}$ near the gun barrel bore surface 114 at the rifled portion 120 of the gun barrel 106 (block 1208). More specifically, the monitoring system 102 may determine the temperature near the gun barrel bore surface 114 in the rifled portion 120 based on Equation 11 above and the example method described in detail below in connection with FIG. 18. After the monitored temperatures T and $T_{re}$ are determined for the non-rifled and rifled portions 118 and 120, the monitoring system 102 may communicate the temperatures (block 1210) to, for example, the central processing system 206 (FIG. 2) or to any other processing system via, for example, the antenna 204 (FIG. 2) Although the operation of block 1210 is shown in the example method of FIG. 12 as occurring unconditionally after determining the monitored temperatures, the example method may be modified so that the temperatures are communicated in response to predetermined events such as, for example, at specified time intervals, when memory is full, or in response to a data request from another processing system (e.g., the central processing system 206).

The monitoring system 102 then determines if the firing regiment of the gun 104 has finished or stopped (block 1212). For example, a gun crew may notify the monitoring system 102 via a gun control system that the gun 104 has finished firing. If the firing regiment has not stopped, control is returned to block 1206 to continue monitoring the temperature near the gun barrel bore surface 114. If the firing regiment has stopped, the monitoring system 102 begins to monitor the erosion of the gun barrel bore surface 114.

Initially, the monitoring system 102 obtains a plurality of time-staggered temperature measurements of the outer surface 112 (FIGS. 1 and 3-5) of the gun barrel 106 using, for example, the temperature transducer 124 (FIGS. 1 and 2) (block 1214). The plurality of time-staggered temperature measurements are used to determine if the gun barrel 106 is in an isothermal condition (block 1216). For example, the time-staggered temperature measurements may be acquired or collected at predetermined time intervals (e.g., one-minute, two-minute, 10-minute, etc. time intervals) to determine when two consecutive time-staggered time temperatures are substantially equal to one another. More specifically, a current time-staggered temperature measurement may be compared to a previously obtained time-staggered temperature measurement, and when two consecutively collected time-staggered temperature measurements are substantially equal, the monitoring system 102 may determine that the gun barrel 106 is in an isothermal condition.

If the monitoring system 102 determines at block 1216 that the gun barrel 106 is not in an isothermal condition, control returns to block 1214 where the monitoring system 102 again obtains one or more time-staggered temperature measurements. If the monitoring system 102 determines at block 1216 that the gun barrel 106 is in an isothermal condition, then the monitoring system 102 determines an amount of erosion in the non-rifled portion 118 of the gun barrel bore surface 114 (block 1218) and the amount of erosion in the rifled portion 120 of the gun barrel bore surface 114 (block 1220). The monitoring system 102 may determine the amount of erosion in the non-rifled and rifled portions 118 and 120 of the gun barrel 106 as described below in connection with FIG. 20.

After determining the amount of erosion of the gun barrel bore surface 114, the monitoring system 102 may communicate the erosion values (block 1222) to, for example, the central processing system 206 (FIG. 2) or to any other processing system via, for example, the antenna 204 (FIG. 2). Although the operation of block 1222 is shown in the example method of FIG. 12 as always happening unconditionally after determining the amounts of erosion, the example method may be modified so that the erosion values are communicated in response to predetermined events such as, for example, at specified time intervals, when memory is full, or in response to a data request from another processing system (e.g., the central processing system 206).

After communicating the erosion values, the monitoring system 102 determines whether to continue monitoring the temperature and erosion of the gun barrel 106 (block 1224). If the monitoring system 102 determines that it should continue to monitor the temperature and erosion, then control is passed back to block 1202. Otherwise, the example method of FIG. 12 is ended. Using a modified version of the example method of FIG. 12, the monitoring system 102 may be recalibrated depending on the amount of erosion (e.g., the erosion determined at blocks 1218 and 1220) that has occurred in the gun barrel bore surface 114 since the last system calibration.

Figure 13:
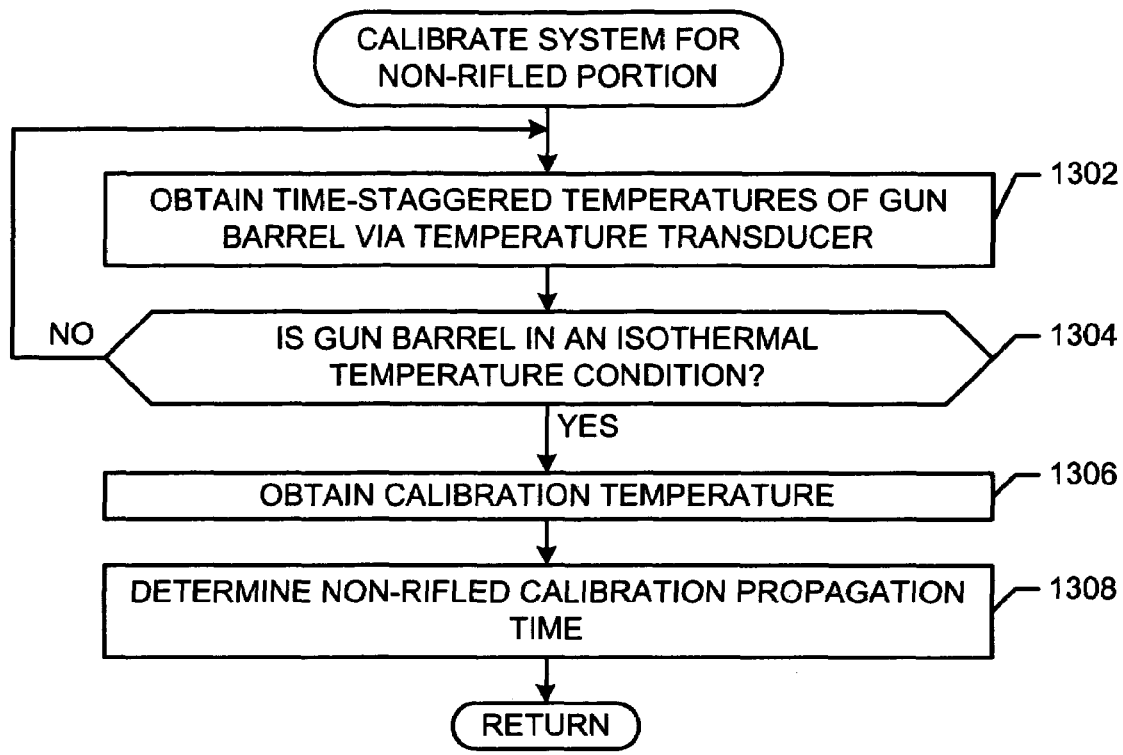
FIG. 13 is a flow diagram of an example method that may be used to calibrate the example temperature and erosion monitoring system of FIG. 1 for monitoring a non-rifled portion of a gun barrel.

FIG. 13 is a flow diagram of an example method that may be used to calibrate the example temperature and erosion monitoring system 102 of FIG. 1 for monitoring a non-rifled portion of a gun barrel (e.g., the non-rifled portion 118 of the gun barrel 106 of FIG. 1). The example method of FIG. 13 may be used to implement the calibrate monitoring system operation of block 1202 of FIG. 12 for the non-rifled portion 118 of the gun barrel 106. The example temperature and erosion monitoring system 102 (FIG. 1) may be configured to implement the example method of FIG. 13 using one or both of the acoustic transducers 126a and 126b.

Initially, the example temperature and erosion monitoring system 102 (FIG. 1) determines if the gun barrel 106 is in an isothermal condition by first obtaining one or more time-staggered temperature measurements of the gun barrel using a temperature transducer (e.g., the temperature transducer 124 of FIGS. 1 and 2) (block 1302). The monitoring system 102 then compares a current or most recently collected temperature measurement to a previously collected temperature measurement to determine if the gun barrel is in an isothermal condition (block 1304). The operations of blocks 1302 and 1304 are substantially similar or identical to the operations of blocks 1214 and 1216 described above in connection with FIG. 12.

If the monitoring system 102 determines that the gun barrel 106 is not in an isothermal condition, then control is passed back to block 1302. However, if the monitoring system 102 determines that the gun barrel 106 is in an isothermal condition, then the monitoring system 102 obtains a calibration temperature $T_C$ of the gun barrel 106 (block 1306). The calibration temperature $T_C$ may be obtained by measuring the temperature of the outer surface 112 of the gun barrel 106 using the temperature transducer 124. The temperature of the outer surface 112 is substantially similar or identical to the temperature of the gun barrel wall 306 (FIG. 3) and the gun barrel bore surface 114 when the gun barrel 106 is in an isothermal condition.

After obtaining the calibration temperature $T_C$ at block 1306, the monitoring system 102 determines the non-rifled calibration propagation time t ($T_C$) of an acoustic wave emitted into the gun barrel wall 306 (e.g., the wall propagation time $t_w$) in the non-rifled portion 118 of the gun barrel 106 (block 1308). The example method of FIG. 14 described in detail below may be used to determine the non-rifled calibration propagation time $t(T_C)$ of block 1308. The non-rifled calibration propagation time $t(T_C)$ can be used in combination with Equations 3, 4, and 5 to form Equation 6 above, which may then be used to determine the temperature near the gun barrel bore surface 114 at the non-rifled portion 118 of the gun barrel 106 as described below in connection with FIG. 17.

Figure 14:
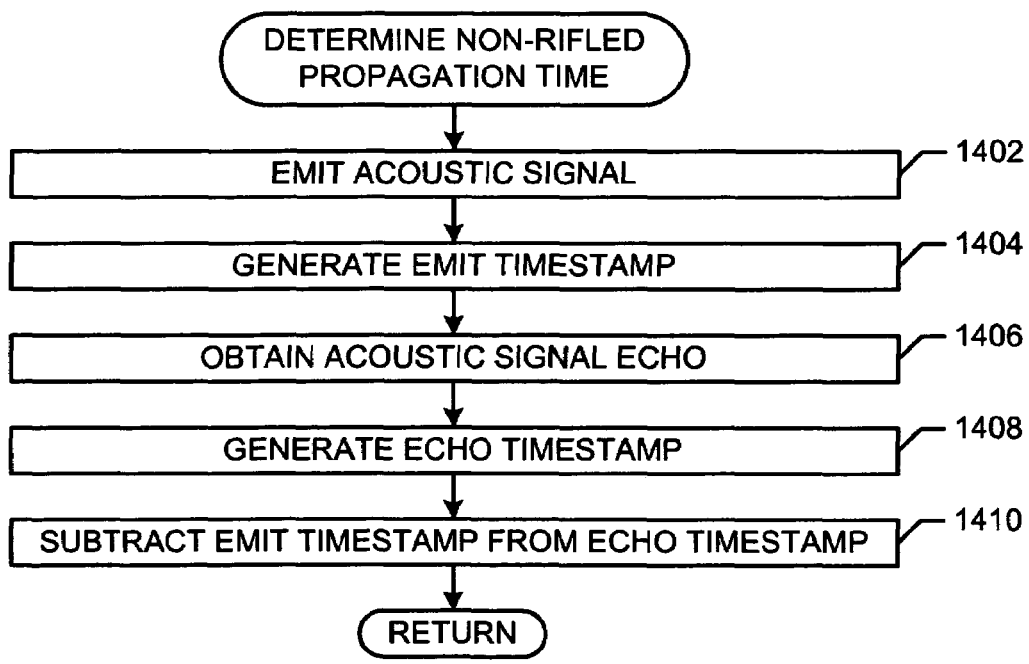
FIG. 14 is a flow diagram of an example method that may be used to determine the propagation time of an acoustic signal that is emitted into a gun barrel wall at a non-rifled portion of a gun barrel.

FIG. 14 is a flow diagram of an example method that may be used to determine propagation time of an acoustic signal (e.g., the acoustic signal 304 of FIG. 3) that is emitted into a gun barrel wall (e.g., the gun barrel wall 306 of FIG. 3) in a non-rifled portion of a gun barrel (e.g., the non-rifled portion 118 of the gun barrel 106 of FIG. 1). The example method of FIG. 14 may be used to implement the operation of block 1308 of FIG. 13, the operation of block 1702 of FIG. 17, and the operation of block 2002 of FIG. 20.

Initially, the example temperature and erosion monitoring system 102 (FIG. 1) emits an acoustic signal (e.g., the acoustic signal 602 of FIG. 6) into the gun barrel wall 306 (FIG. 3) (block 1402). Specifically, the monitoring system 102 emits the acoustic signal 602 via one of the acoustic transducers 126 (FIGS. 1-5). The monitoring system 102 then generates a timestamp corresponding with the time at which the monitoring system 102 emitted the acoustic signal 602 (block 1404). Although the operation of block 1404 is shown in the flow diagram of FIG. 14 as occurring after the acoustic signal 602 is emitted, emission of the acoustic signal 602 and generation of the emit timestamp may occur substantially simultaneously or at substantially the same time. Alternatively, the emit timestamp may be generated prior to emitting the acoustic signal 602 and used to trigger the monitoring system 102 to emit the acoustic signal 602 at the particular time indicated by the emit timestamp.

The monitoring system 102 then obtains an acoustic signal echo (e.g., the acoustic echo 606 of FIGS. 6 and 7) (block 1406), which is associated with the acoustic signal emitted at block 1402. More specifically, as described in greater detail above in connection with FIGS. 5-7, after emitting the acoustic signal 602, the acoustic signal 602 propagates through the gun barrel wall 306 (FIG. 3) and is reflected by the gun barrel bore surface 114 of the non-rifled portion 118 of the gun barrel 106 to create the acoustic echo 606.

The monitoring system 102 generates an echo timestamp (block 1408) corresponding to the time at which the monitoring system 102 obtained the acoustic echo 606. The monitoring system 102 then subtracts the emit timestamp from the echo timestamp (block 1410) to determine the propagation time of an acoustic signal through the gun barrel wall 306 (FIG. 3) in the non-rifled portion 118 of the gun barrel 106. When the example method of FIG. 14 is used to implement the operation of block 1308 of FIG. 13, the example method may be used to determine the non-rifled calibration propagation time $t(T_C)$. When the example method of FIG. 14 is used to implement the operations of block 1702 of FIG. 17 and block 2002 of FIG. 20, the example method may be used to determine the non-rifled monitoring propagation time t(T). After determining the propagation time at block 1410, control is returned to, for example, a calling function or process such as one of the example methods of FIGS. 13, 17, or 20.

Figure 15:
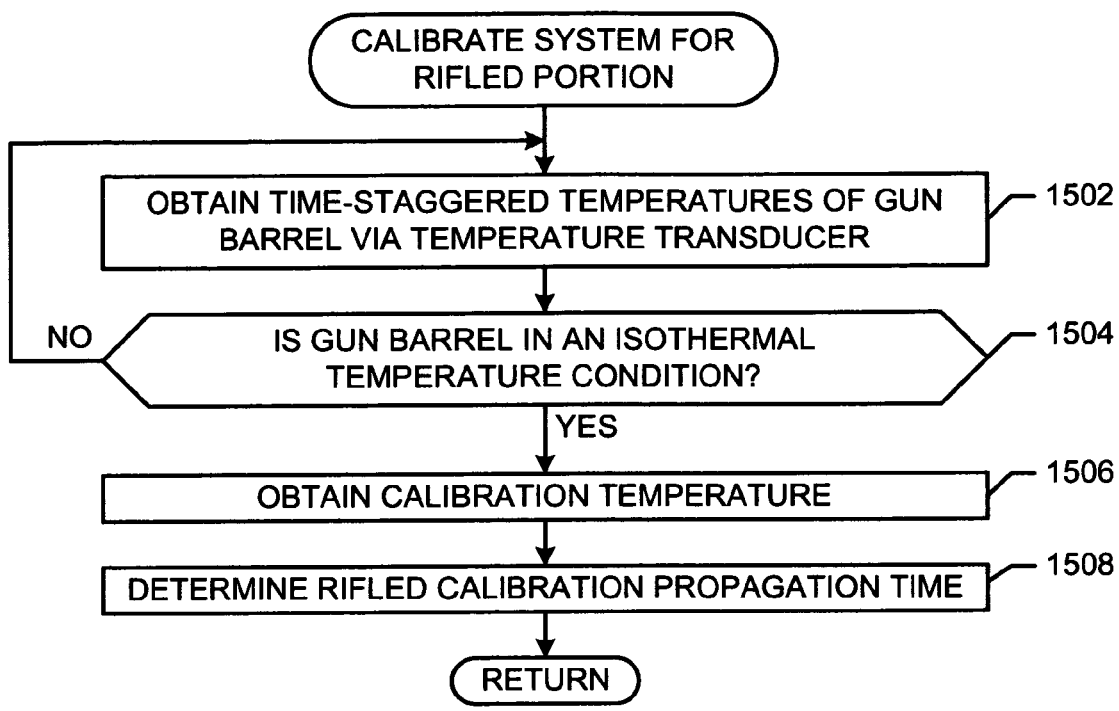
FIG. 15 is a flow diagram of an example method that may be used to calibrate the example temperature and erosion monitoring system of FIG. 1 for monitoring a rifled portion of a gun barrel.

FIG. 15 is a flow diagram of an example method that may be used to calibrate the example temperature and erosion monitoring system 102 of FIG. 1 for monitoring a rifled portion of a gun barrel (e.g., the rifled portion 120 of the gun barrel 106 of FIG. 1). The example method of FIG. 15 may be used to implement the calibrate monitoring system operation of block 1202 of FIG. 12 for the rifled portion 120 of the gun barrel 106. The example temperature and erosion monitoring system 102 (FIG. 1) may be configured to implement the example method of FIG. 15 using one or both of the acoustic transducers 126c and 126d.

Initially, the example temperature and erosion monitoring system 102 determines if the gun barrel 106 is in an isothermal condition by first obtaining one or more time-staggered temperature measurements of the gun barrel 106 using a temperature transducer (e.g., the temperature transducer 124 of FIGS. 1 and 2) (block 1502). The monitoring system 102 then determines if the gun barrel 106 is in an isothermal condition (block 1504) by comparing a current or most recently collected temperature measurement to a previously collected temperature measurement. The operations of blocks 1502 and 1504 are substantially similar or identical to the operations of blocks 1214 and 1216 described above in connection with FIG. 12.

If the monitoring system 102 determines that the gun barrel 106 is not in an isothermal condition, then control is passed back to block 1502. However, if the monitoring system 102 determines that the gun barrel 106 is in an isothermal condition, then the monitoring system 102 obtains a calibration temperature $T_C$ of the gun barrel 106 (block 1506). The calibration temperature $T_C$ may be obtained by measuring the temperature of the outer surface 112 of the gun barrel 106 using the temperature transducer 124. The temperature of the outer surface 112 is substantially similar or identical to the temperature of the gun barrel wall 306 (FIG. 3) and the gun barrel bore surface 114 when the gun barrel 106 is in an isothermal condition.

After obtaining the calibration temperature at block 1506, the monitoring system 102 determines the rifled calibration propagation time $t_{re}(T_C)$ of an acoustic wave emitted into the gun barrel wall 306 in the rifled portion 120 of the gun barrel 106 (block 1508). The example method of FIG. 16 described in detail below may be used to determine the rifled calibration propagation time $t_{re}(T_C)$ of block 1508. The rifled calibration propagation time $t_{re}(T_C)$ can be used in combination with Equations 8, 9, and 10 to form Equation 11 above, which may then be used to determine the temperature near the gun barrel bore surface 114 in the rifled portion 120 of the gun barrel 106 as described below in connection with FIG. 18.

Figure 16:
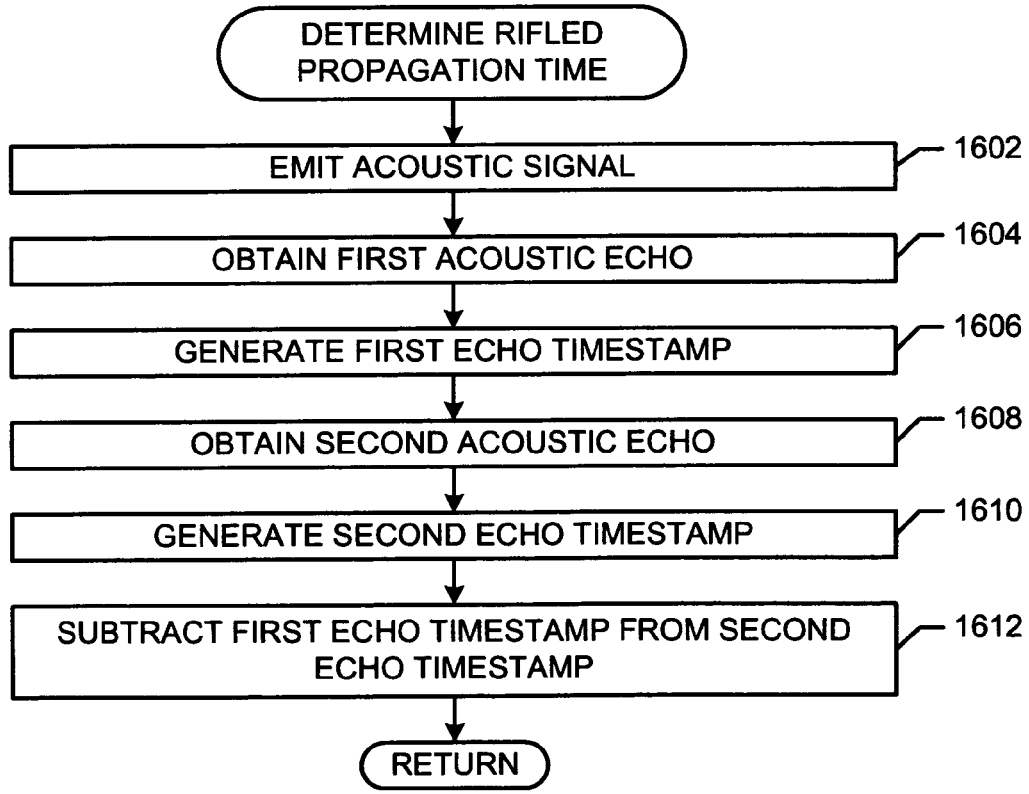
FIG. 16 is a flow diagram of an example method that may be used to determine the propagation time of an acoustic signal that is emitted into a gun barrel wall at a rifled portion of a gun barrel.

FIG. 16 is a flow diagram of an example method that may be used to determine the propagation time of an acoustic signal that is emitted into a gun barrel wall (e.g., the gun barrel wall 306 of FIG. 3) at a rifled portion of a gun barrel (e.g., the rifled portion 120 of the gun barrel 106 of FIG. 1). The example method of FIG. 16 may be used to implement the operation of block 1508 of FIG. 15, the operation of block 1802 of FIG. 18, and the operation of block 2002 of FIG. 20. The example temperature and monitoring system 102 (FIG. 1) may be configured to implement the example method using one or both of the acoustic transducers 126c and 126d of FIGS. 1 and 2.

Initially, the monitoring system 102 emits an acoustic signal (e.g., the acoustic signal 602 of FIG. 6) into the gun barrel wall 306 (FIG. 3) (block 1602). Specifically, the monitoring system 102 emits the acoustic signal 602 via one of the acoustic transducers 126 (FIGS. 1-5).

The monitoring system 102 then obtains a first acoustic echo (e.g., the first acoustic echo 604 of FIGS. 6 and 7) (block 1604), which is associated with the acoustic signal 602 emitted at block 1602. More specifically, as described in greater detail above in connection with FIGS. 4, 6, and 7, after emitting the acoustic signal 602, the acoustic signal 602 propagates through the gun barrel wall 306 (FIG. 3) and is partially reflected by the first land 406 (FIG. 4) of the rifled portion 120 of the gun barrel 106 to create the first acoustic echo 604. The monitoring system 102 then generates a first echo timestamp (block 1606) corresponding to the time at which the monitoring system 102 obtained the first acoustic echo 604.

The monitoring system 102 then obtains a second acoustic echo (e.g., the second acoustic echo 606 of FIGS. 6 and 7) (block 1604), which is associated with the acoustic signal 602 emitted at block 1602. More specifically, as described in greater detail above in connection with FIGS. 4, 6, and 7, after a portion of the acoustic signal 602 is partially reflected by the first land 406, another portion of the acoustic signal 602 propagates toward the second land 408 (FIG. 4) and is reflected by the second land 408 to create the second acoustic echo 606. The monitoring system 102 then generates a second echo timestamp (block 1610) corresponding to the time at which the monitoring system 102 obtained the second acoustic echo 606.

The monitoring system 102 then subtracts the second echo timestamp from the first echo timestamp (block 1612) to determine the propagation time of the acoustic signal 602 through the rifling element 302 (FIGS. 3 and 4). When the example method of FIG. 16 is used to implement the operation of block 1508 of FIG. 15, the example method is used to determine the rifled calibration propagation time $t_{re}(T_C)$. When the example method of FIG. 16 is used to implement the operations of block 1802 of FIG. 18 and block 2002 of FIG. 20, the example method may be used to determine the rifled monitoring propagation time $t_{re}(T)$. After determining the propagation time at block 1410, control is returned to, for example, a calling function or process such as one of the example methods of FIGS. 15, 18, or 20.

Figure 17:
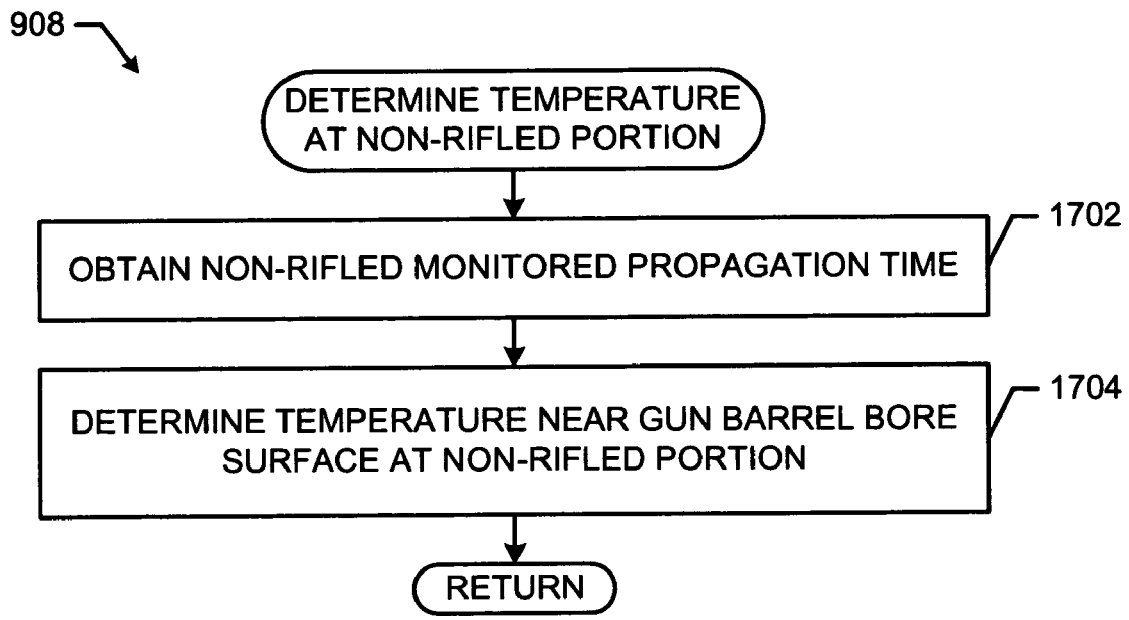
FIG. 17 is a flow diagram of an example method that may be used to determine a temperature near a gun barrel bore surface at a non-rifled portion of a gun barrel using acoustic signals.

FIG. 17 is a flow diagram of an example method that may be used to determine a temperature of a gun barrel (e.g., the gun barrel 106) near a gun barrel bore surface (e.g., the gun barrel bore surface 114 of FIGS. 1 and 5) at a non-rifled portion (e.g., the non-rifled portion 118 FIG. 1) of the gun barrel using acoustic signals. The example method of FIG. 17 may be used to implement the operation of block 1206 of FIG. 12. The example temperature and erosion monitoring system 102 (FIG. 1) may be configured to implement the example method of FIG. 17 using one or both of the acoustic transducers 126a and 126b (FIGS. 1 and 2).

Initially, the monitoring system 102 determines a non-rifled monitored propagation time t(T) (block 1702). The non-rifled monitored propagation time t(T) may be obtained using the example method described above in connection with FIG. 14. The monitoring system 102 then determines a temperature near the gun barrel bore surface 114 at the non-rifled portion 118 of the gun barrel 106 (block 1704). The monitoring system 102 may determine the temperature as described below in connection with FIG. 19. After determining the gun barrel temperature at the non-rifled portion 118, control is returned to, for example, a calling function or process such as the example method of FIG. 12.

Figure 18:
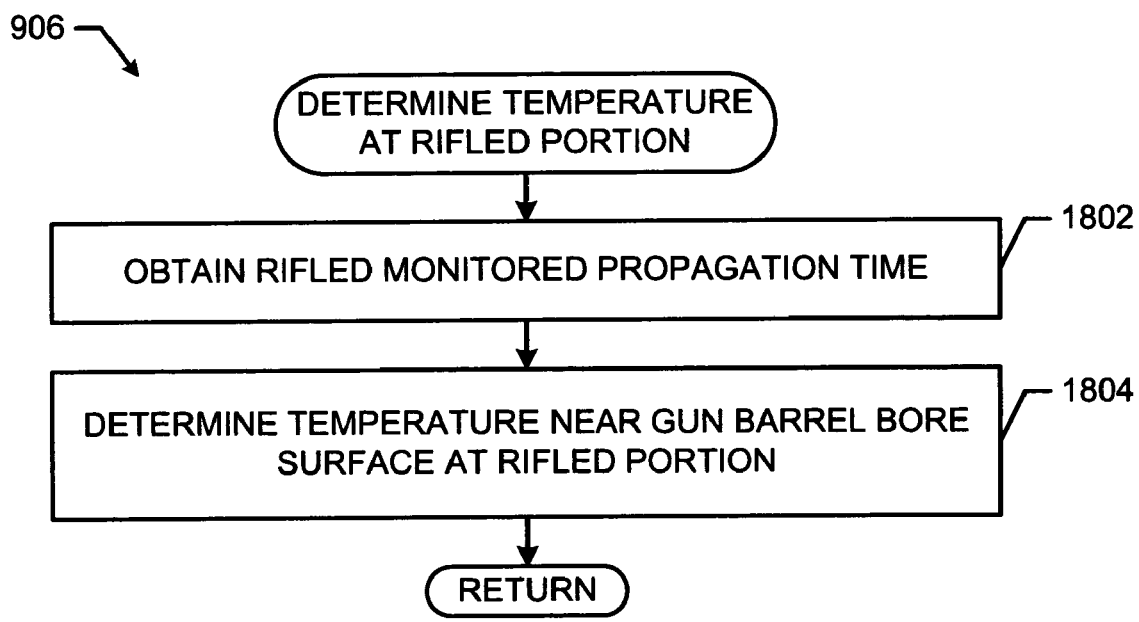
FIG. 18 is a flow diagram of an example method that may be used to determine a temperature near a gun barrel bore surface at a rifled portion of a gun barrel using acoustic signals.

FIG. 18 is a flow diagram of an example method that may be used to determine a temperature of a gun barrel (e.g., the gun barrel 106) near a gun barrel bore surface (e.g., the gun barrel bore surface 114 of FIGS. 1 and 5) at a rifled portion of a gun barrel (e.g., the rifled portion 120 of the gun barrel 106 of FIG. 1) using acoustic signals. The example method of FIG. 18 may be used to implement the operation of block 1208 of FIG. 12. The example temperature and erosion monitoring system 102 (FIG. 1) may be configured to implement the example method of FIG. 18 using one or both of the acoustic transducers 126c and 126d (FIGS. 1 and 2).

Initially, the monitoring system 102 determines a rifled monitored propagation time $t_{re}(T)$ (block 1802). The rifled monitored propagation time $t_{re}(T)$ may be obtained using the example method described above in connection with FIG. 16. The monitoring system 102 then determines the temperature near the gun barrel bore surface 114 at the rifled portion 120 of the gun barrel 106 (block 1804). For example, the monitoring system 102 may determine the temperature using the example method described below in connection with FIG. 19. After determining the gun barrel temperature at the rifled portion 120, control is returned to, for example, a calling function or process such as the example method of FIG. 12.

Figure 19:
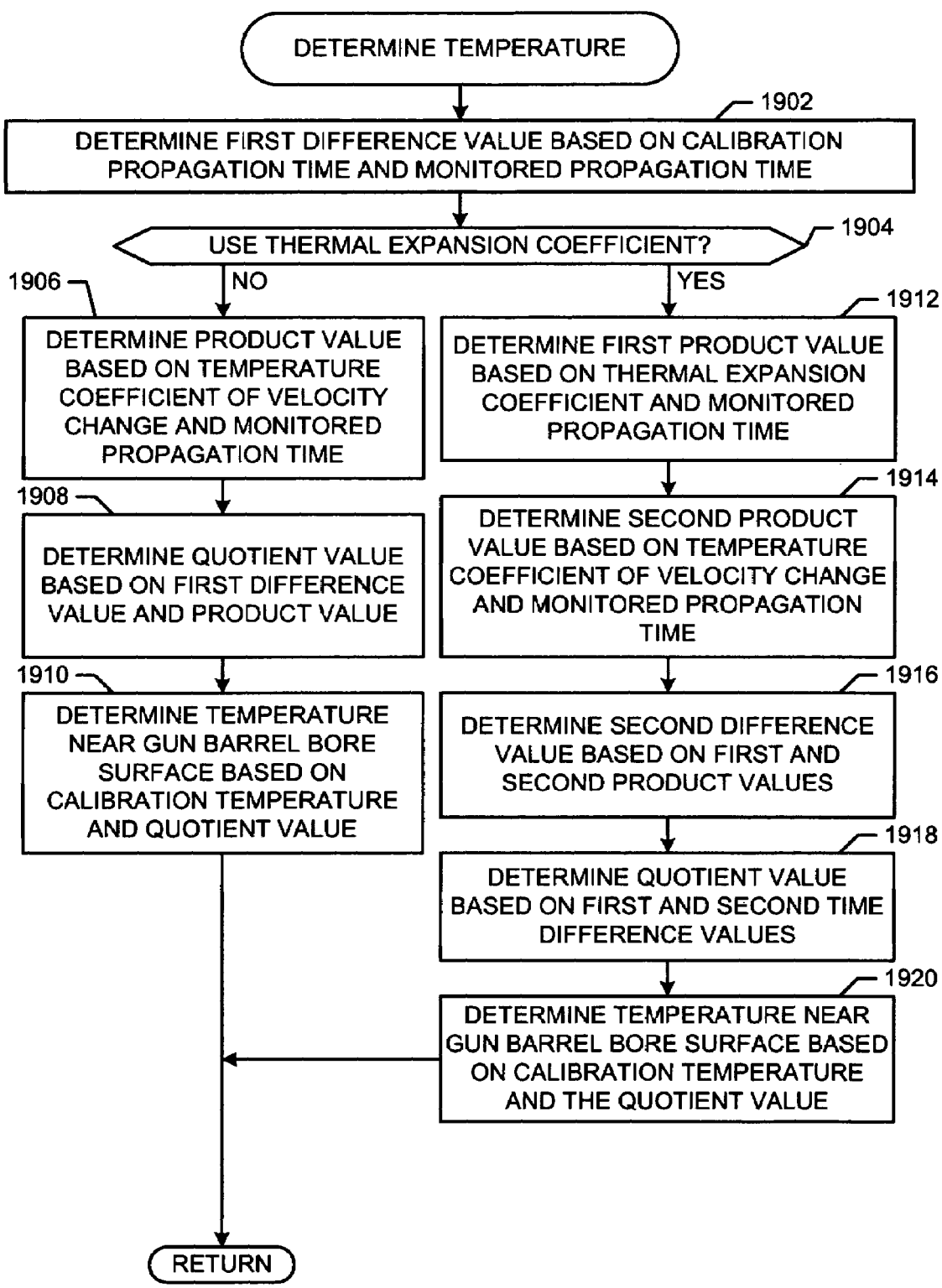
FIG. 19 is a flow diagram of an example method that may be used to determine the temperature near a gun barrel bore surface based on information collected using acoustic signals.

FIG. 19 is a flow diagram of an example method that may be used to determine a temperature of a gun barrel (e.g., the gun barrel 106) near a gun barrel bore surface (e.g., the gun barrel bore surface 114 of FIG. 1) based on information collected using acoustic signals (e.g., the acoustic waves 304 of FIG. 3 and 602, 604, and 606 of FIGS. 6 and 7). The example method of FIG. 19 may be implemented using the example temperature and erosion monitoring system 102 (FIG. 1). Alternatively, the central processing system 206 (FIG. 2) may be configured to obtain acoustic propagation information from the monitoring system 102 and to implement the example method.

The example method of FIG. 19 may be used to determine the temperature near the gun barrel bore surface 114 (FIG. 1) for the non-rifled portion 118 and the rifled portion 120 of the gun barrel 106. For example, the example method may be used to determine the temperature near the gun barrel bore surface 114 at the non-rifled portion 118 using the non-rifled calibration propagation time $t(T_C)$ determined in connection with block 1308 of the example method of FIG. 13, the non-rifled monitored propagation time $t(T)$ determined in connection with block 1702 of the example method of FIG. 17, and Equation 6 described above. The example method may be used to determine the temperature near the gun barrel bore surface 114 in the rifled portion 120 using the rifled calibration propagation time $t_{re}(T_C)$ determined in connection with block 1508 of the example method of FIG. 15, the rifled monitored propagation time $t_{re}(T_C)$ determined in connection with block 1802 of the example method of FIG. 18, and Equation 11 described above.

Initially, the monitoring system 102 determines a first difference value (e.g., one of the difference values $(t(T_C)-t(T))$ or $(t_{re}(T_C)-t_{re}(T))$ of Equations 6 and 11, respectively) based on a calibration propagation time (e.g., one of the calibration propagation times $t(T_C)$ and $t_{re}(T_C)$ determined above in connection with the example methods of FIGS. 13 and 15, respectively) and a monitored propagation time (e.g., one of the monitored propagation times $t(T)$ and $t_{re}(T)$ obtained above in connection with the example methods of FIGS. 17 and 18, respectively) (block 1902). For example, if the example method is used to determine the temperature T at the non-rifled portion 118 (using Equation 6 and the example method of FIG. 17), the monitoring system 102 may determine the first difference value $(t(T_C)-t(T))$ by subtracting the non-rifled monitored propagation time $t(T)$ from the non-rifled calibration propagation time $t(T_C)$. Alternatively, if the example method of FIG. 19 is used to determine the rifled portion temperature $T_{re}$ (using Equation 11 and the example method of FIG. 18), the monitoring system 102 may determine the first difference value $(t_{re}(T_C)-t_{re}(T))$ by subtracting the rifled monitored propagation time $t_{re}(T)$ from the rifled calibration propagation time $t_{re}(T_C)$.

The monitoring system 102 then determines whether to use the thermal expansion coefficient EB to determine the temperature near the gun barrel bore surface 114 (block 1904). If the monitoring system 102 is configured to not use the thermal expansion coefficient EB, then the monitoring system 102 determines a product value based on the temperature coefficient of velocity change $y_f$ and a monitored propagation time (e.g., one of the monitored propagation times $t(T)$ and $t_{re}(T)$ obtained above in connection with the example methods of FIGS. 17 and 18, respectively) (block 1906). For example, if the example method of FIG. 19 is used to determine the non-rifled temperature T at the non-rifled portion 118 (using Equation 6 and the example method of FIG. 17), the monitoring system 102 may multiply the temperature coefficient of velocity change $y_f$ by the non-rifled monitored propagation time $t(T)$ to determine the product value $(y_f \cdot t(T))$. Alternatively, if the example method is used to determine the rifled portion temperature $T_{re}$ (using Equation 11 and the example method of FIG. 18), the monitoring system 102 may multiply the temperature coefficient of velocity change $y_f$ by the rifled monitored propagation time $t_{re}(T)$ to determine the product value $(y_f \cdot t_{re}(T))$.

The monitoring system 102 then determines a quotient value based on the first difference value determined at block 1902 (e.g., one of the propagation time difference values $(t(T_C)-t(T))$ or $(t_{re}(T_C)-t_{re}(T))$) and the product value determined at block 1906 (e.g., one of the product values $(y_f \cdot t(T))$ or $(y_f \cdot t_{re}(T))$) (block 1908). For example, if the example method of FIG. 19 is used to determine the non-rifled portion temperature T (using Equation 6 and the example method of FIG. 17), the monitoring system 102 may determine the quotient value $$\frac{(t(T_C) - t(T))}{(y_f \cdot t(T))}$$

by dividing the first difference value $(t(T_C)-t(T))$ by the product value $(y_f \cdot t(T))$. Alternatively, if the example method of FIG. 19 is used to determine the rifled portion temperature $T_{re}$ (using Equation 11 and the example method of FIG. 18), the monitoring system 102 may divide the first difference value $(t_{re}(T_C)-t_{re}(T))$ by the product value $(y_f \cdot t_{re}(T))$ to determine the quotient value $$\frac{(t_{re}(T_C) - t_{re}(T))}{(y_f \cdot t_{re}(T))}.$$

The monitoring system 102 then determines the temperature near the gun barrel bore surface 114 based on the calibration temperature $T_C$ and the quotient value determined at block 1908 (e.g., one of the quotient values $$\frac{(t(T_C) - t(T))}{(y_f \cdot t(T))} \text{ or } \frac{(t_{re}(T_C) - t_{re}(T))}{(y_f \cdot t_{re}(T))}$$

(block 1910). For example, if the example method is used to determine the non-rifled portion temperature T (using Equation 6 and the example method of FIG. 17), the monitoring system 102 may determine the non-rifled temperature T by adding the calibration temperature $T_C$ to the quotient value $$\frac{(t(T_C) - t(T))}{(y_f \cdot t(T))}$$

as shown above in Equation 6. Alternatively, if the example method is used to determine the rifled portion temperature $T_{re}$ (using Equation 11 and the example method of FIG. 18), the monitoring system 102 may determine the rifled portion temperature $T_{re}$ by adding the calibration temperature $T_C$ to the quotient value $$\frac{(t_{re}(T_C) - t_{re}(T))}{(y_f \cdot t_{re}(T))}.$$

After the monitoring system 102 has determined the temperature near the gun barrel bore surface 114, control is returned to, for example, a calling function or process such as the example method of FIG. 12.

If the monitoring system 102 determines at block 1904 to use the thermal expansion coefficient EB, then the monitoring system 102 proceeds to the operation of block 1912. As described above, the monitoring system 102 generally uses the thermal expansion coefficient EB to determine the gun barrel temperature at the non-rifled portion 118 of the gun barrel 106. Although the thermal expansion coefficient EB may be used to determine a thermal expansion compensated temperature at the non-rifled portion 118 or the rifled portion 120, the following describes determining a thermal expansion compensated gun barrel temperature near the gun barrel bore surface 114 at the non-rifled portion 118 of the gun barrel 106. Of course, although not described in detail, one or more of the operations of the example method of FIG. 19 described below may be modified or rearranged to determine the gun barrel temperature in the rifled portion 120 of the gun barrel 106 using the thermal expansion coefficient EB.

After the monitoring system 102 determines at block 1904 to use the thermal expansion coefficient EB to determine a thermal expansion compensated gun barrel temperature $T_E$ in the non-rifled portion 118 of the gun barrel 106, the monitoring system 102 determines a first product value based on the thermal expansion coefficient EB and the non-rifled monitored propagation time t(T) (block 1912). More specifically, as shown in Equation 15 above, the monitoring system 102 determines the first product value (EB·t(T)) by multiplying the thermal expansion coefficient EB by the non-rifled monitored propagation time t(T).

The monitoring system 102 then determines a second product value based on the temperature coefficient of velocity change $y_f$ and the non-rifled monitored propagation time t(T) (block 1914). Specifically, as shown above in Equation 13, the monitoring system 102 may determine the second product value ($y_f$·t(T)) by multiplying the temperature coefficient of velocity change $y_f$ by the non-rifled monitored propagation time t(T).

The monitoring system 102 may then determine a second propagation difference value based on the first and second product values determined above in connection with blocks 1912 and 1914 (block 1916). The monitoring system 102 may determine the second difference value ($y_f$·t(T)−EB·t(T)) as shown above in Equation 15 by subtracting the first product value (EB·t(T)) from the second product value ($y_f$·t(T)).

After determining the second difference value, the monitoring system 102 may determine a quotient value based on the first and second time difference values determined above in connection with blocks 1902 and 1916, respectively (block 1918). The monitoring system 102 may determine the quotient value $$\frac{(t(T_C) - t(T))}{(y_f \cdot t(T) - EB \cdot t(T))}$$

as shown above in Equation 15 by dividing the first difference value (t($T_C$)−t(T)) by the second difference value ($y_f$·t(T)−EB·t(T)).

After determining the quotient value, the monitoring system 102 may determine the temperature of the gun barrel near the gun barrel bore surface 114 at the non-rifled portion 118 of the gun barrel 106 based on the quotient value determined at block 1918 and the calibration temperature $T_C$ (block 1920). The monitoring system 102 may determine the non-rifled gun barrel bore temperature near the gun barrel bores surface 114 by adding the calibration temperature $T_C$ to the quotient value $$\frac{(t(T_C) - t(T))}{(y_f \cdot t(T) - EB \cdot t(T))}$$

as shown above in Equation 15. After the monitoring system 102 has determined the temperature at the non-rifled portion 118, control is returned to, for example, a calling function or process such as the example method of FIG. 12.

Figure 20:
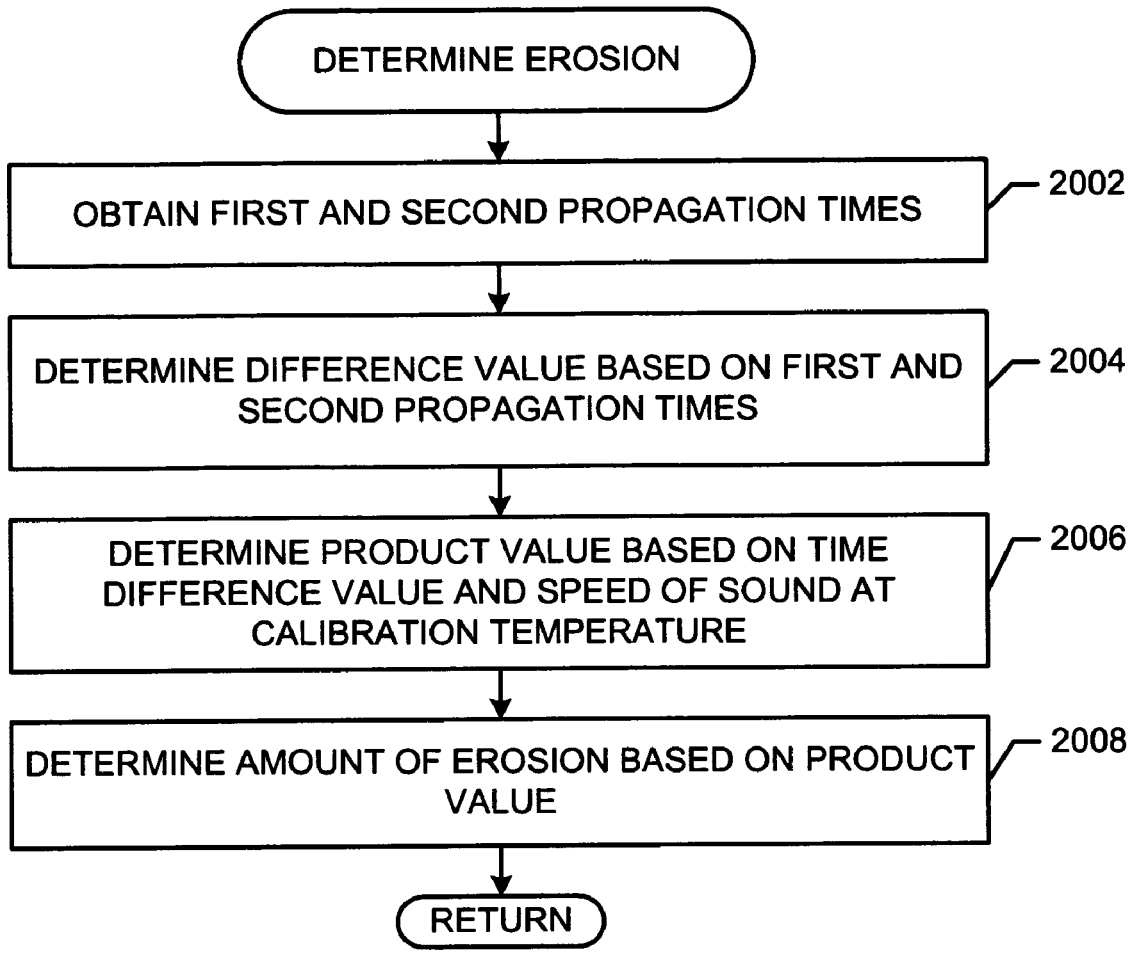
FIG. 20 is a flow diagram of an example method that may be used to determine an amount of erosion of a gun barrel bore surface.

FIG. 20 is a flow diagram of an example method that may be used to determine an amount of erosion E of a gun barrel bore surface (e.g., the gun barrel bore surface 114 of FIGS. 1 and 3-5). The example method of FIG. 20 may be adapted to determine the amount of erosion ϵ at the non-rifled portion 118 and the rifled portion 120 of the gun barrel 106 based on Equation 17 above. For example, the monitoring system 102 and one or both of the acoustic transducers 126a and 126b (FIGS. 1 and 2) may be configured to determine the amount of erosion ϵ of the gun barrel bore surface 114 at the non-rifled portion 118 using the example method of FIG. 20. In addition, the monitoring system 102 and one or both of the acoustic transducers 126c and 126d (FIGS. 1 and 2) may be configured to determine the amount of erosion ϵ of the gun barrel bore surface 114 at the rifled portion 120 using the example method of FIG. 20.

Initially, the monitoring system 102 obtains first and second propagation times $t_1$(T,0) and $t_2$(T, ϵ) (block 2002). The first and second propagation times $t_1$(T,0) and $t_2$(T, ϵ) are obtained during isothermal conditions of the gun barrel bore 106. The temperature of the gun barrel 106 when it is in an isothermal condition may be substantially equal to the calibration temperature $T_C$. For example, as shown above in connection with Equation 17, the first and second propagation times $t_1$($T_C$,0) and $t_2$($T_C$, ϵ) are collected when the gun barrel bore 106 is at the calibration temperature $T_C$. Specifically, the first propagation time $t_1$($T_C$,0) is determined prior to firing one or more rounds. The second propagation time $t_2$($T_C$, ϵ) is determined after firing the one or more rounds, and is associated with the amount of erosion ϵ of the gun barrel bore surface 114 due to firing the one or more rounds. The monitoring system 102 may determine an amount of erosion ϵ of the gun barrel bore surface 114 based on an analysis of the first and second propagation times $t_1$($T_C$,0) and $t_2$($T_C$, ϵ). To measure erosion ϵ in the non-rifled portion 118, the monitoring system 102 may obtain the first and second propagation times $t_1$($T_C$,0) and $t_2$($T_C$, ϵ) using the example method described above in connection with FIG. 14. In this case, the propagation times $t_1$($T_C$,0) and $t_2$($T_C$, ϵ) correspond to the amount of time $t_w$ (FIG. 5) required by an acoustic signal (e.g., the acoustic signal 602 of FIG. 6) to propagate through a gun barrel wall thickness $d_w$ (FIG. 5). To measure erosion ϵ in the rifled portion 120, the monitoring system 102 may obtain the first and second propagation times $t_1$($T_C$,0) and $t_2$($T_C$, ϵ) using the example method described above in connection with FIG. 16. In this case, the propagation times $t_1(T_C,0)$ and $t_2(T_C, \epsilon)$ correspond to the amount of time required by an acoustic signal (e.g., the acoustic signal 602 of FIG. 6) to propagate through one of the rifling elements 302 (FIGS. 3 and 4).

Using the first and second propagation times $t_1(T_C,0)$ and $t_2(T_C, \epsilon)$, the monitoring system 102 determines the amount of erosion $\epsilon$ of the gun barrel bore surface 114 based on Equation 17 above as described below in connection with blocks 2004, 2006, and 2008. After obtaining the first and second propagation times $t_1(T_C,0)$ and $t_2(T_C, \epsilon)$ the monitoring system 102 determines a difference value based on the first and second propagation times $t_1(T_C,0)$ and $t_2(T_C, \epsilon)$ (block 2004). Specifically, as shown above in Equation 17, the monitoring system 102 subtracts the second propagation time $t_2(T_C, \epsilon)$ from the first propagation time $t_1(T_C,0)$ to determine the difference value $(t(T_C,0)-t(T_C, \epsilon))$.

The monitoring system 102 then determines a product value based on the difference value $(t(T_C,0)-t(T_C,\epsilon))$ and the calibration temperature speed of sound $V(T_C)$ (block 2006). Specifically, as shown above in Equation 17, the monitoring system 102 multiplies the time difference value $(t(T_C,0)-t(T_C,\epsilon))$ by the speed of sound $V(T_C)$ to determine the product value $V(T_C) \cdot (t(T_C,0)-t(T_C, \epsilon))$. The monitoring system 102 then determines the amount of erosion E based on the product value $V(T_C) \cdot (t(T_C,0)-t(T_C,\epsilon))$ (block 2008). Specifically, as shown above in Equation 17, the monitoring system 102 divides the product value $V(T_C) \cdot (t(T_C,0)-t(T_C,\epsilon))$ by two to determine the amount of erosion $\epsilon$. After determining the amount of erosion $\epsilon$, control may be returned to, for example, a calling function or process such as one implemented using the example method of FIG. 12.

FIG. 21 is a functional block diagram of an example system 2100 that may be used to implement the apparatus, methods, and articles of manufacture described herein. The structures shown in FIG. 21 may be implemented using any desired combination of hardware and/or software. For example, one or more integrated circuits, discrete semiconductor components, or passive electronic components may be used. Additionally or alternatively, some or all, or parts thereof, of the structures of FIG. 21 may be implemented using instructions, code, or other software and/or firmware, etc. stored on a computer-readable medium that, when executed by, for example, a processor system (e.g., the processor system 2210 of FIG. 22), perform the methods disclosed herein.

In general, the example system 2100 may be configured to monitor the temperature and erosion conditions of an elongated member (e.g., the gun barrel 106 of FIG. 1) having a cavity (e.g., the gun barrel bore 116 of FIG. 1) therein. For example, the example system 2100 may be used to implement the example temperature and erosion monitoring system 102 (FIG. 1) based on the example methods described above in connection with FIGS. 12 through 20 and sequences of operations configured at least in part according to Equations 1 through 17 above.

Now turning in detail to FIG. 21, the example system 2100 includes a data interface 2102, a temperature transducer 2104, acoustic transducers 2106, an acoustic transducer driver 2108, an analog-to-digital converter 2110, a propagation time analyzer 2112, a temperature monitor 2114, and an erosion monitor 2116, all of which may be communicatively coupled as shown. The data interface 2102 may be configured to obtain and store calibration values and/or data constants (e.g., the calibration temperature $T_C$, the temperature coefficient of velocity change $y_\beta$, the thermal expansion coefficient EB, the calibration temperature speed of sound $V(T_C)$, etc.), and any other value associated with the example methods described herein such as, for example, propagation times, temperature values, erosion values, etc. The data interface 2102 may be configured to communicate information to and receive information from the temperature and erosion monitors 2114 and 2116. The data interface 2102 may also be configured to obtain triggers and timing event commands to coordinate operations in the example system 2100. For example, the data interface 2102 may be configured to trigger the acoustic transducers 2106 to emit acoustic signals or waves. Additionally, the data interface 2102 may also be configured to obtain temperature information from the temperature transducer 2104. The data interface 2102 may also be configured to communicate with another data processing system such as, for example, the central processor system 206 of FIG. 2. In this manner, the data interface 2102 may communicate temperature and erosion measurements to the central data processing system 206.

The temperature transducer 2104 may be substantially similar or identical to the temperature transducer 124 of FIGS. 1 and 2. For example, the temperature transducer 124 may be implemented using any type of temperature transducer technology such as, for example, a thermocouple, an infrared temperature sensor, etc. The temperature transducer 2104 may be configured to be mechanically coupled or engaged to the outer surface 112 of the gun barrel 106, acquire calibration temperatures $T_C$, and communicate those calibration temperatures to the data interface 2102. Although one temperature transducer is shown, the example system 2100 may include any number of temperature transducers.

The acoustic transducers 2106 may be configured to emit acoustic signals or waves (e.g., the acoustic signals 304 (FIG. 3) and 602 (FIG. 6)) and detect acoustic signals or waves (e.g., the echoes 604 and 606 of FIG. 6). The acoustic transducers 2106 may be configured to be mechanically coupled to or otherwise engage the outer surface 112 of the gun barrel 106 and may be substantially similar or identical to the acoustic transducers 126 of FIGS. 1 and 2. For example, the acoustic transducers 2106 may be implemented using, for example, any contact or non-contact ultrasonic technology. Some example ultrasonic technologies include piezoelectric devices, laser generation devices, Electromagnetic Acoustic Transduction (EMAT) devices, and spark gap devices. The acoustic transducers 2106 may include transceivers and/or separate emitters and receivers.

The acoustic transducer driver 2108 may be configured to generate electrical signals and cause the acoustic transducers 2106 to emit acoustic signals or waves based on those electrical signals. The acoustic transducer driver 2108 may receive trigger events or timing events from the data interface 2102 indicating when to drive the acoustic transducers 2106. The acoustic transducer driver 2108 may be implemented using an ultrasonic transducer driver such as, for example, a 30 MHz ultrasonic signal generator or any other ultrasonic signal generator.

The analog-to-digital converter (ADC) 2110 may be configured to obtain analog electrical signals from the acoustic transducers 2106 that correspond to acoustic waves or signals detected by the acoustic transducers 2106 (e.g., the echoes 604 and 606 of FIG. 6). Additionally, the ADC 2110 may convert the analog electrical signals to digital information (i.e., a digital representation of an acoustic wave) and communicate the digital information to the propagation time analyzer 2112. The ADC 2110 may be implemented using a high-speed digitization device such as, for example, a 1 gigahertz digitizer, a 5 gigahertz digitizer, etc.

The propagation time analyzer 2112 may be configured to obtain the digital information from the ADC 2110 that corresponds to acoustic signals or waves detected by the acoustic transducers 2106. The propagation time analyzer 2112 may be configured to implement the example methods described above in connection with FIGS. 14 and 16. For example, the propagation time analyzer 2112 may generate timestamp information regarding reception of acoustic signals and may obtain emit timestamps from the data interface 2101 corresponding to acoustic signal trigger events that cause the acoustic transducers 2106 to emit acoustic signals or waves. The propagation time analyzer 2112 may then determine propagation times (e.g., the calibration propagation times $t(T_C)$, monitored propagation times $t(T)$, etc.) as described above. The propagation time analyzer 2112 may determine propagation times using any one or more of a number of known signal processing algorithms. For example, the propagation time analyzer 2112 may be configured to determine the propagation times using at least one of peak detection, cross-correlation, matched filter methods, and sweep frequency/inverse filtering methods (e.g., chirp). The propagation time analyzer 2112 may communicate the propagation times to the temperature and erosion monitors 2114 and 2116.

The temperature monitor 2114 may be configured to determine temperatures near the gun barrel bore surface 114 based on the propagation times obtained from the propagation time analyzer 2112 and other values (e.g., calibration values and constant values) obtained from the data interface 2102. For example, the temperature monitor 2114 may be configured to implement the example methods described above in connection with FIGS. 17 through 19 and/or one or more sequences of mathematical operations associated with one or more of Equations 1 through 15 described above. The temperature monitor 2114 may communicate temperature values to the data interface 2102.

The erosion monitor 2116 may be configured to determine amounts of erosion on the gun barrel bore surface 114 based on the propagation times obtained from the propagation time analyzer 2112 and other values (e.g., calibration values and constant values) obtained from the data interface 2102. For example, the erosion monitor 2116 may be configured to implement the example method described above in connection with FIG. 21 and/or one or more sequences of mathematical operations associated with Equation 16 and 17 described above. The erosion monitor 2116 may communicate erosion values to the data interface 2102.

Figure 22:
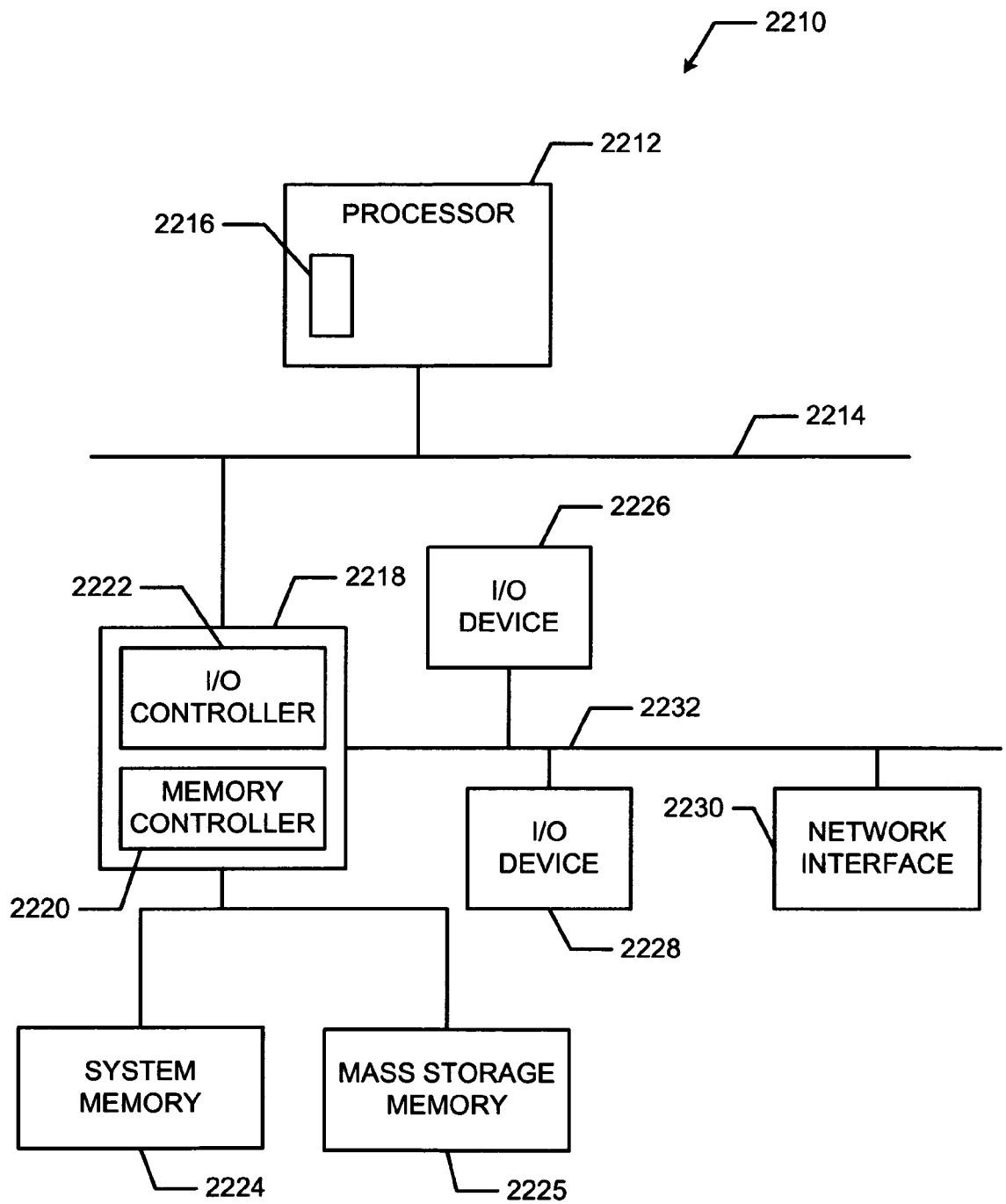
FIG. 22 is a block diagram of an example processor system that may be used to implement the methods, systems, and apparatus described herein.

FIG. 22 is a block diagram of an example processor system 2210 that may be used to implement the apparatus and methods described herein. As shown in FIG. 22, the processor system 2210 includes a processor 2212 that is coupled to an interconnection bus 2214. The processor 2212 includes a register set or register space 2216, which is depicted in FIG. 22 as being entirely on-chip, but which could alternatively be located entirely or partially off-chip and directly coupled to the processor 2212 via dedicated electrical connections and/or via the interconnection bus 2214. The processor 2212 may be any suitable processor, processing unit or microprocessor. Although not shown in FIG. 22, the system 2210 may be a multi-processor system and, thus, may include one or more additional processors that are identical or similar to the processor 2212 and that are communicatively coupled to the interconnection bus 2214.

The processor 2212 of FIG. 22 is coupled to a chipset 2218, which includes a memory controller 2220 and an input/output (I/O) controller 2222. As is well known, a chipset typically provides I/O and memory management functions as well as a plurality of general purpose and/or special purpose registers, timers, etc. that are accessible or used by one or more processors coupled to the chipset 2218. The memory controller 2220 performs functions that enable the processor 2212 (or processors if there are multiple processors) to access a system memory 2224 and a mass storage memory 2225.

The system memory 2224 may include any desired type of volatile and/or non-volatile memory such as, for example, static random access memory (SRAM), dynamic random access memory (DRAM), flash memory, read-only memory (ROM), etc. The mass storage memory 2225 may include any desired type of mass storage device including hard disk drives, optical drives, tape storage devices, etc.

The I/O controller 2222 performs functions that enable the processor 2212 to communicate with peripheral input/output (I/O) devices 2226 and 2228 and a network interface 2230 via an I/O bus 2232. The I/O devices 2226 and 2228 may be any desired type of I/O device such as, for example, a keyboard, a video display or monitor, a mouse, etc. The network interface 2230 may be, for example, an Ethernet device, an asynchronous transfer mode (ATM) device, an 802.11 device, a DSL modem, a cable modem, a cellular modem, etc. that enables the processor system 2210 to communicate with another processor system.

While the memory controller 2220 and the I/O controller 2222 are depicted in FIG. 22 as separate functional blocks within the chipset 2218, the functions performed by these blocks may be integrated within a single semiconductor circuit or may be implemented using two or more separate integrated circuits.

Although certain methods, apparatus, and articles of manufacture have been described herein, the scope of coverage of this patent is not limited thereto. To the contrary, this patent covers all methods, apparatus, and articles of manufacture fairly falling within the scope of the appended claims either literally or under the doctrine of equivalents.

What is claimed is:

1. A method of monitoring a condition of a cavity surface of an elongated member having a cavity therein, comprising:

emitting a first ultrasonic signal that propagates from a first surface of an elongated member having a cavity therein toward a second surface of the cavity, wherein the second surface has a first temperature value;

obtaining first and second echoes associated with the first ultrasonic signal, wherein at least one of the first and second echoes is associated with a recess in the second surface; and determining a second temperature value based on the first and second echoes and the first temperature value to monitor the condition of the second surface, wherein the second temperature value is associated with the temperature of the second surface.

2. A method as defined in claim 1, wherein the second temperature value is associated with an average temperature between the first surface and the second surface of the elongated member.

3. A method as defined in claim 1, further comprising:

emitting a second ultrasonic signal that propagates from the first surface toward the second surface, wherein the temperature of the second surface is substantially equal to the second temperature value;

obtaining third and fourth echoes associated with the second ultrasonic signal, wherein at least one of the third and fourth echoes is associated with the recess;

determining a first propagation time based on the first and second echoes;

determining a second propagation time based on the third and fourth echoes; and determining the second temperature value based on the first and second propagation times and the first temperature value.

4. A method as defined in claim 1, wherein the elongated member is a gun barrel.

5. A method as defined in claim 1, wherein the cavity surface is a gun barrel bore surface.

6. A method as defined in claim 1, wherein the first temperature value is at least one of a calibration temperature value or an isothermal temperature value.

7. A method as defined in claim 1, wherein the recess in the second surface comprises a channel in the second surface.

8. A method as defined in claim 1, further comprising:
emitting a second ultrasonic signal that propagates from the first surface toward the second surface, wherein the temperature of the second surface is substantially equal to the first temperature value;
obtaining third and fourth echoes associated with the second ultrasonic signal, wherein at least one of the third and fourth echoes is associated with the recess;
determining a first propagation time based on the first and second echoes;
determining a second propagation time based on the third and fourth echoes; and
determining an amount of erosion of the second surface based on the first and second propagation times.

9. A method as defined in claim 8, wherein determining the amount of erosion of the second surface further comprises:
generating a difference value by subtracting the second propagation time from the first propagation time;
generating a product value based on the difference value and a velocity of sound value; and
determining the amount of erosion by dividing the product value by two.

10. An apparatus to monitor a condition of a cavity surface of an elongated member having a cavity therein, comprising:
a transducer configured to emit a first ultrasonic signal that propagates from a first surface of an elongated member having a cavity therein toward a second surface of the cavity, wherein the second surface has a first temperature value, wherein the transducer is configured to obtain first and second echoes associated with the first ultrasonic signal, and wherein at least one of the first and second echoes is associated with a recess in the second surface; and
a temperature monitor configured to determine a second temperature value based on the first and second echoes and the first temperature value to monitor the condition of the second surface, wherein the second temperature value is associated with the temperature of the second surface.

11. An apparatus as defined in claim 10, wherein the second temperature value is associated with an average temperature between the first surface and the second surface of the elongated member.

12. An apparatus as defined in claim 10, further comprising a time analyzer configured to determine a first propagation time based on the first and second echoes, wherein the transducer is configured to emit a second ultrasonic signal that propagates from the first surface toward the second surface, wherein the temperature of the second surface is substantially equal to the second temperature value, wherein the transducer is configured to obtain third and fourth echoes associated with the second ultrasonic signal, wherein at least one of the third and fourth echoes is associated with the recess, wherein the time analyzer is configured to determine a second propagation time based on the third and fourth echoes, and wherein the temperature monitor is configured to determine the second temperature value based on the first and second propagation times and the first temperature value.

13. An apparatus as defined in claim 10, wherein the elongated member is a gun barrel.

14. An apparatus as defined in claim 10, wherein the cavity surface is a gun barrel bore surface.

15. An apparatus as defined in claim 10, wherein the first temperature value is at least one of a calibration temperature value or an isothermal temperature value.

16. An apparatus as defined in claim 10, wherein the recess in the second surface comprises a channel in the second surface.

17. An apparatus as defined in claim 10, further comprising:
a time analyzer configured to determine a first propagation time based on the first and second echoes, wherein the transducer is configured to emit a second ultrasonic signal that propagates from the first surface toward the second surface, wherein the temperature of the second surface is substantially equal to the first temperature value, wherein the transducer is configured to obtain third and fourth echoes associated with the second ultrasonic signal, wherein at least one of the third and fourth echoes is associated with the recess, wherein the time analyzer is configured to determine a second propagation time based on the third and fourth echoes; and
an erosion monitor configured to determine an amount of erosion of the second surface based on the first and second propagation times.

18. An apparatus as defined in claim 17, wherein the erosion monitor is configured to determine the amount of erosion of the second surface by:
generating a difference value by subtracting the second propagation time from the first propagation time;
generating a product value based on the difference value and a velocity of sound value; and
determining the amount of erosion by dividing the product value by two.

19. A machine accessible medium having instructions stored thereon that, when executed, cause a machine to:
emit a first ultrasonic signal that propagates from a first surface of an elongated member having a cavity therein toward a second surface of the cavity, wherein the second surface has a first temperature value;
obtain first and second echoes associated with the first ultrasonic signal, wherein at least one of the first and second echoes is associated with a recess in the second surface; and
determine a second temperature value based on the first and second echoes and the first temperature value to monitor the condition of the second surface, wherein the second temperature value is associated with the temperature of the second surface.

20. A machine accessible medium as defined in claim 19, wherein the second temperature value is associated with an average temperature between the first surface and the second surface of the elongated member.

21. A machine accessible medium as defined in claim 19 having instructions stored thereon that, when executed, cause the machine to:
emit a second ultrasonic signal that propagates from the first surface toward the second surface, wherein the temperature of the second surface is substantially equal to the second temperature value;
obtain third and fourth echoes associated with the second ultrasonic signal, wherein at least one of the third and fourth echoes is associated with the recess;
determine a first propagation time based on the first and second echoes;

determine a second propagation time based on the third and fourth echoes; and determine the second temperature value based on the first and second propagation times and the first temperature value.

22. A machine accessible medium as defined in claim 19, wherein the elongated member is a gun barrel.

23. A machine accessible medium as defined in claim 19, wherein the cavity surface is a gun barrel bore surface.

24. A machine accessible medium as defined in claim 19, wherein the first temperature value is at least one of a calibration temperature value or an isothermal temperature value.

25. A machine accessible medium as defined in claim 19, wherein the recess in the second surface comprises a channel in the second surface.

26. A machine accessible medium as defined in claim 19 having instructions stored thereon that, when executed, cause the machine to:

emit a second ultrasonic signal that propagates from the first surface toward the second surface, wherein the temperature of the second surface is substantially equal to the first temperature value;

obtain third and fourth echoes associated with the second ultrasonic signal, wherein at least one of the third and fourth echoes is associated with the recess;

determine a first propagation time based on the first and second echoes;

determine a second propagation time based on the third and fourth echoes; and determine an amount of erosion of the second surface based on the first and second propagation times.

27. A machine accessible medium as defined in claim 26 having instructions stored thereon that, when executed, cause the machine to:

generate a difference value by subtracting the second propagation time from the first propagation time;

generate a product value based on the difference value and a velocity of sound value; and determine the amount of erosion by dividing the product value by two.

* * * * *